United States Patent [19]
Zhang et al.

[11] Patent Number: 5,384,397
[45] Date of Patent: Jan. 24, 1995

[54] TETRAPHENYLPORPHYRIN COMPOUNDS AND METHOD

[75] Inventors: Xumu Zhang, Mountain View, Calif.; Erich Uffelman, Lexington, Va.; James P. Collman, Palo Alto, Calif.

[73] Assignee: The Board of Trustees of the Leland Stanford Junior University, Stanford, Calif.

[21] Appl. No.: 149,207

[22] Filed: Nov. 9, 1993

Related U.S. Application Data

[63] Continuation-in-part of Ser. No. 973,030, Nov. 9, 1992, Pat. No. 5,274,090.

[51] Int. Cl.⁶ ................ C01B 13/00; C01B 13/18; C07B 47/00
[52] U.S. Cl. .................................. 540/143; 540/460; 540/455
[58] Field of Search ........................................ 540/143

[56] References Cited

U.S. PATENT DOCUMENTS

| | | | |
|---|---|---|---|
| 4,609,383 | 9/1986 | Bonaventura et al. | 33/16 |
| 4,629,544 | 12/1986 | Bonaventura et al. | 204/131 |
| 4,761,209 | 8/1988 | Bonaventura et al. | 204/129 |
| 4,952,289 | 8/1990 | Ciccone et al. | 204/129 |
| 4,959,135 | 9/1990 | Zenner et al. | 204/129 |
| 5,017,274 | 5/1991 | Kerr et al. | 204/129 |
| 5,096,724 | 3/1992 | Zenner et al. | 424/124 |

FOREIGN PATENT DOCUMENTS

| | | | |
|---|---|---|---|
| 0066884A2 | 6/1982 | European Pat. Off. | 55/16 |
| 0110396A2 | 11/1983 | European Pat. Off. | 55/16 |
| 0439387A2 | 1/1991 | European Pat. Off. | 55/16 |

OTHER PUBLICATIONS

Bulach, V., et al., "The High-Yield Synthesis and Characterization of the First Porphyrin-Cyclam Dinucleating Ligand and Its Iron(III)/Copper(II) Complex," Angew. Chem. Int. Ed. Engl. 30(5):572–575 (1991).

Caron, C., et al., "Models for the Reduced States of Cytochrome P-450 and Chloroperoxydase. Structures of a Pentacoordinate High-Spin Iron(II) Mercaptide Mesoporphyrin Derivative and Its Carbonyl Adduct," J. Am. Chem. Soc. 101(24):7401–7402 (1979).

Chang, C. K., "Stacked Double-Macrcyclic Ligands. 1. Sythesis of a 'Crowned' Porphyrin," J. Am. Chem. Soc. 99:2819–2822 (1977).

Collman, J. P., et al., "Synthesis, Characterization, and X-ray Structure of the Ruthenium 'Picnic-Basket' Porphyrins," J. Am. Chem. Soc. 110:3477–3486 (1988).

Collman, J. P., et al., "Reversible Binding of Dinitrogen and Dioxygen by a Ruthenium 'Picnic-Basket' Porphyrin," J. Am. Chem. Soc. 110:3486–3495 (1988).

Collman. J. P., et al., "O₂ and CO Binding to Iron (II) Porphyrins: A Comparison of the 'Picket Fence' and 'Pocket' Porphyrins," J. Am. Chem. Soc. 105:3052–3064 (1983).

De Castro, E. S., "Breathing Underwater," Chemtech Nov., pp. 682–687 (1990).

Doppelt, P., et al., "Synthetic Analogs for the Active Site of Cytochrome P 450. Synthesis, Spectroscopic Properties and X-ray Structures of a Five-Coordinate Thiolato-Cobalt II-Meso-Tetra-(αααα-o-Pivalamidophenyl) Porphyrin Complex and Its Di-oxygen Adduct," New J. Chem. 11(4):357–364 (1987).

Hashimoto, T., et al., "Ligand, Oxygen, and Carbon Monoxide Affinities of Iron(II) Modified 'Capped' Porphyrins," J. Am. Chem. Soc. 104: 2101–2109 (1982).

Linard, J. E., et al., "Oxygenation of Iron(II) and Cobalt (II) 'Capped' Porphyrins," J. Am. Chem. Soc. 102(6):1896–1904 (1980).

Momenteau, M., and Lavalette, D., "Kinetic Evidence for Di-oxygen Stabilization in Oxygenated Iron(II)–Porphyrins by Distal Polar Interactions," J. Chem. Soc., Chem. Commun., pp. 341–343 (1982).

MomentHeau, M., et al., "Iron (II) 'Hanging Imidazole' Porphyrin: Synthesis and Proximal Ligand Effect on CO and O₂ Binding," J. Chem. Soc., Chem. Commun., pp. 962–964 (1983).

Schappacher, M., et al., "Synthesis, structure and spectroscopic properties of two models for the active site of the oxygenated state of cytochrome P540," Am. J. Biochem. 168:419–429 (1987).

Smith, J. R. L., and Lower, R. J., "The Mechanism of the Reaction between t-Butyl Hydroperoxide and 5,10,15,20–Tetra(N–methyl–4–pyridyl)porphyrinatoiron(III) Pentachloride in Aqueous Solution," J. Chem. Soc. Perkin Trans. 2:31–39 (1991).

Tatsuno, Y., et al., "A Model Complex for the Active Site of Cytochrome P–450," Inorganica Chimica Acta 152:5–7 (1988).

Traylor, T. G., et al., "Steric Effects in CO, O₂, and RNC Binding," J. Am. Chem. Soc. 107:604–614 (1985).

Uemori, Y., and Kyuno, E., "O₂ and CO Binding to 'Jellyfish' Type Iron(II) Porphyrins," Inorg. Chem. 28:1690–1694 (1989).

*Primary Examiner*—Robert T. Bond
*Attorney, Agent, or Firm*—Peter J. Dehlinger; Vincent M. Powers

[57] ABSTRACT

The invention includes a water-soluble oxygen carrier. The oxygen carrier includes a meso-α,α,α,α-tetrakis(o-propanoylamino)phenylporphyrin, in which the 3-carbons of the propanoyl groups are each covalently bound to an amine nitrogen, and iron or cobalt is bound to the pyrrole nitrogens of the porphyrin. The oxygen carrier also includes a ligand L for protecting the open face of the porphyrin from μ-oxo dimer formation.

14 Claims, 12 Drawing Sheets

XII

XIII

TETRAPHENYLPORPHYRIN COMPOUNDS AND METHOD

The present application is a continuation-in-part of U.S. patent application Ser. No. 07/973,030 filed Nov. 9, 1992 new U.S. Pat. No. 5,274,090, which is incorporated herein by reference.

Portions of the research conducted in support of the present invention were sponsored by the National Institutes of Health, Grant No. GM17880.

FIELD OF THE INVENTION

The present invention relates to porphyrin compounds as oxygen carriers and as agents for binding carbon monoxide.

REFERENCES

Almog, J., et al., *J. Am Chem.* 97:226–227 (1975)
Almog, J., et al., *Tetrahedron* 37: 3589–3601 (1981).
Baldwin, J. E., et al., *J. Chem. Soc., Dalton Trans.* pp. 1739–1746 (1984).
Battersby, A. R., et al., *J. Chem. Soc., Chem. Comm.* pp. 879–891 (1976).
Battersby, A. R., et al., *Tetrahedron Lett.* 3169–3172 (1978).
Boitrel, B., et al., *J. Chem. Soc. Chem. Comm.* pp. 1820 (1985).
Collman, J. P., et al., *J. Am. Chem. Soc.* 95:7868–7870 (1973).
Collman, J. P., et al., *J. Am. Chem. Soc.* 97:1427–1439 (1975).
Collman, J. P., et al., *J. Am. Chem. Soc.* 100:2761–2766 (1978).
Collman, J. P., et al., *J. Am. Chem. Soc.* 103: 2450–2452 (1981).
Collman, J. P., et al., *Inorg. Chem.* 22:2:1427–1432 (1983).
Collman, J. P., et al., *J. Am. Chem. Soc.* 110:3477–3486 (1988).
De Castro, E. S. (1990) *Chemtech* (1990) November, pp. 682–687.
Diekmann, H., et al., *J. Am. Chem. Soc.* 93:4068–4070 (1971).
Elliott, C. M. (1980) *Anal. Chem.* 52: 666–668.
Hashimoto, T., et al. *J. Am. Chem. Soc.* 104:2101–2109 (1982).
Izatt et al. Chem. Rev. 91, 1721–2085 (1991).
Labat, G., and Meunier, B.sLaba *J. Org. Chem.* 54, 5008–5011 (1989).
Lecas, A., et al., *Tetrahedron Lett.* pp. 1019–1022 (1985).
Linard, J. E., et al., *J. Am. Chem. Soc.* 102:1896–1904. (1980).
Lindsey, J. (1980) *J. Org. Chem.* 45:5215.
Momenteau, M., et al., *Nouv. J. Chim.* 3:77–99 (1979)
Momenteau, M., et al., *J. Mol. Catal.* 7:315–320 (1980).
Momenteau, M., et al., *J. Chem. Soc. Perkins Trans.* 1:189–196 (1983).
Smith, J. R. L., and Lower, R. J. *J. Chem. Soc. Perkin Trans.* 2:31–39 (1991).
Sorrell, T. N. (1980) *Inorg. Synth.* 20:161–169.
Traylor, T. G., et al., *J. Am. Chem. Soc.* 107:604–614 (1985).
Uemori, Y., et al., *Inorg. Chem.* 28:1690–1694 (1989).

BACKGROUND OF THE INVENTION

A variety of synthetic porphyrins designed to mimic oxygen carriers have been proposed. Some examples include "capped" porphyrins (Almog, 1975, 1981; Baldwin), "bridged" porphyrins (Battersby, 1976, 1978); "picket fence" porphyrins (Collman, 1973, 1975), "pocket" porphyrins (Collman, 1981, 1983), "basket-handle" porphyrins (Momenteau, 1979, 1980, 1983), "gyroscope" porphyrins (Lecas, Boitrel), "cyclophane" porphyrins (Diekman, Traylor), and "jelly-fish" type porphyrins (Uemori).

In general, structures such as noted above include a porphyrin ring which is bound to a transition metal such as iron or cobalt, and an axial ligand which protects one of the axial coordination sites of the metal from irreversible oxidation processes. In some structures, the ligand is covalently attached to the porphyrin ring. However, such covalent attachment requires multistep synthetic reaction schemes that are lengthy or produce the desired compound in low overall yield. More typically, the axial ligand is not covalently attached to the porphyrin. In such cases, where the porphyrin compound is used in a liquid, the ligand is included in the liquid, usually in a 100- to 1000-fold excess relative to the porphyrin compound, to ensure saturation of the axial coordination site of the metal. In other cases, where the porphyrin compound is contained in a dry solid phase, the ligand can be provided by the solid phase itself, thereby linking the porphyrin compound to the solid phase.

It is well known that the affinities of axial ligands for porphyrin metals vary according to the nature of the particular ligand. The ligand is usually selected not only to protect the metal from oxidation, but also to modulate the relative affinity of the porphyrin metal for a selected small molecule such as oxygen or carbon monoxide. Nitrogen-containing ligands such as imidazoles and pyridines are known to bind relatively strongly to porphyrin metals (e.g., iron and cobalt), whereas other ligands, such as thiolates, typically bind weakly, and are needed in high concentrations (for liquid applications) to attain high axial site occupancy. Moreover, since the binding of ligands to porphyrin metals is reversible, the porphyrin is constantly, albeit transiently, susceptible to irreversible oxidation during the time that ligand is not bound to the axial site. It would therefore be desirable to provide a porphyrin complex in which the affinity for the axial ligand is enhanced, but without invoking covalent attachment of the ligand to the porphyrin.

In addition, there has been interest in the development of water-soluble oxygen carriers. U.S. Pat. Nos. 4,602,987, 4,609,383, and 4,629,544 disclose the use of water-soluble, porphyrin-containing proteins such as hemoglobin for extracting oxygen from fluids. Subsequent to the issue of those patents, however, it has been reported that the large molecular weight of hemoglobin, its limited water solubility, and the high overpotentials needed in redox reactions with hemoglobin place serious limitations on such use (De Castro, 1990).

Ideally, a water-soluble oxygen carrier or binding compound should be easy to synthesize, have a high oxygen-binding affinity and yet be amenable to deoxygenation under selected conditions, be resistant to oxidative degradation, and be able to withstand heating without isomerization.

SUMMARY OF THE INVENTION

The present invention includes, in one aspect, a water-soluble oxygen carrier. The oxygen carrier includes a meso-α,α,α,α-tetrakis(o-propanoylamino)phenylporphyrin, in which the 3-carbons of the propanoyl groups are each covalently bound to an amine nitrogen, and iron or cobalt is bound to the pyrrole nitrogens of the porphyrin. The oxygen carrier also includes a ligand L for protecting the open face of the porphyrin from μ-oxo dimer formation. The oxygen carrier contains one or more amine nitrogens which, in preferred embodiments, are secondary amine nitrogens, tertiary amine nitrogens, or, in another embodiment, for imparting permanent positive charge, are quaternary amine nitrogens.

Also forming part of the invention is a method of forming a water-soluble oxygen carrier such as described in the preceding paragraph. The method includes (a) reacting meso-α,α,α,α-tetrakis-(o-aminophenyl)porphyrin with acryloyl chloride or acryloyl bromide to produce a tetraacrylamide porphyrin, (b) reacting the tetraacrylamide porphyrin with an amine to produce a meso-e,α,α,α,α-tetrakis(o-(3-aminopropanoylamino)phenyl)porphyrin derivative, and (c) inserting into the thus-formed porphyrin, a metal selected from the group consisting of iron and cobalt. In one embodiment, prior to insertion of the metal, the 3-amino groups in the meso-α,α,α,α-tetrakis(o-(3-aminopropanoylamino)phenyl)porphyrin derivative may be converted to quaternary amines by alkylation.

These and other objects and features of the invention will become more fully apparent when the following detailed description of the invention is read in conjunction with the accompanying drawings.

DETAILED DESCRIPTION OF THE INVENTION

I. Definitions

The terms defined below will have the following meaning, unless otherwise stated:

A "tetraphenylporphyrin" or "meso-tetraphenylporphyrin" consists of a porphyrin ring having the backbone shown below:

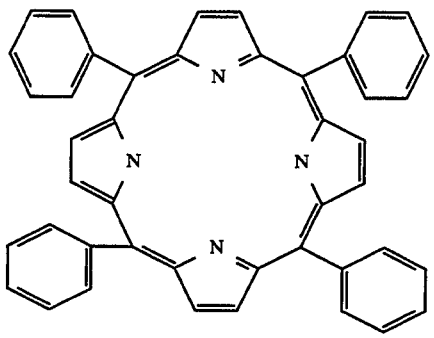

A "crown" or crown ether" refers to a cyclic polyether in which one or more ether oxygens may be substituted with a protonated nitrogen or sulfur atom, and which has a capacity to form multiple hydrogen bonds with a hydrogen bond donor such as a primary amine.

A "Soret band" refers to a UV-visible absorption band which is characteristic of thiolate-iron(II)-heme-carbon monoxide complexes. The maximal absorbance of such a band occurs between about 440–455 nm.

II. Porphyrin-Crown Complexes

Figure 1:
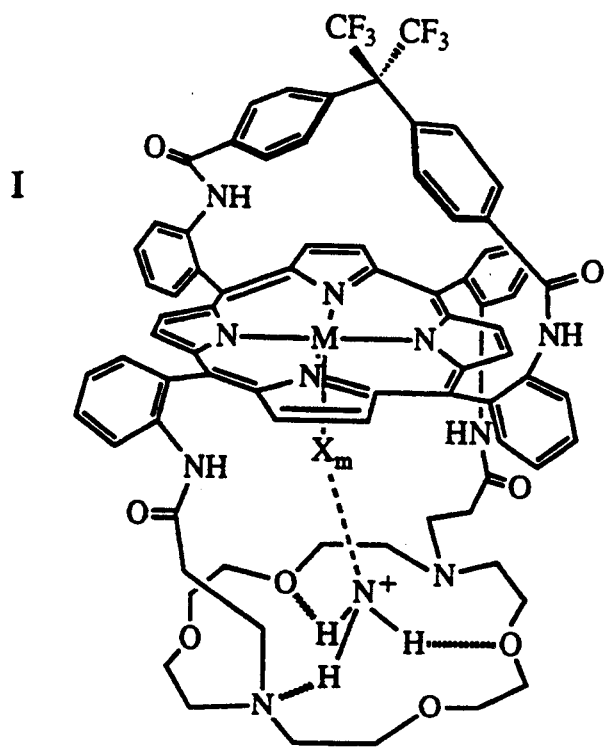
FIG. 1 shows a metalloporphyrin-crown complex of the present invention.

A metalloporphyrin-crown ligand complex of the present invention is shown in FIG. 1. The complex includes a tetraphenylporphyrin that has, on one side, a crown ether, and on the other side, a bridge structure. The crown ether (also referred to herein as "crown") is rigidly attached to the tetraphenylporphyrin by spacer arms, shown as propanoylamino moieties in the figure, linking the nitrogen atoms of the crown to two diagonally opposing phenyl groups. The bridge structure, exemplified by a 2,2-bis(4-ketophenyl)hexafluoropropane moiety in FIG. 1, also covalently links to one another two diagonally opposing phenyl groups, but on the side of the porphyrin opposite that of the crown. A metal M, such as iron or cobalt, is bound to the pyrrole nitrogens of the porphyrin.

According to an important aspect of the invention, the complex also includes a ligand that is held by the crown ether such that a metal-binding atom $X_m$ (e.g., a thiolate or an imidazole nitrogen) in the ligand is axially coordinated to the metal. The ligand additionally includes a crown ether-binding group (e.g., an amine in FIG. 1) that can be held noncovalently and with high affinity by the crown ether, thereby facilitating binding of group $X_m$ to metal M.

Figure 2:
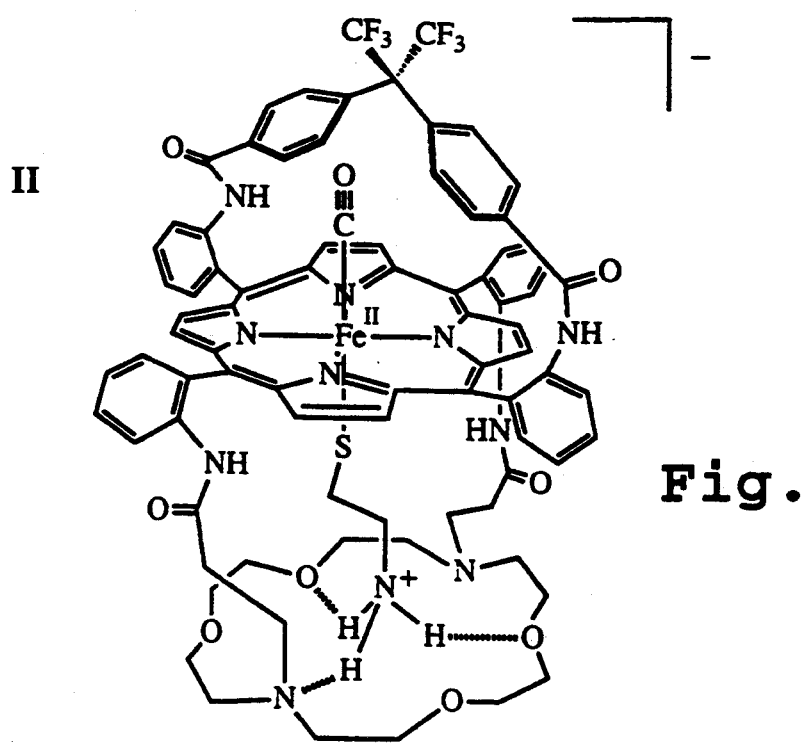
FIG. 2 shows the carbon monoxide adduct of a porphyrin metal-thiolate complex of the present invention.
Figure 7:
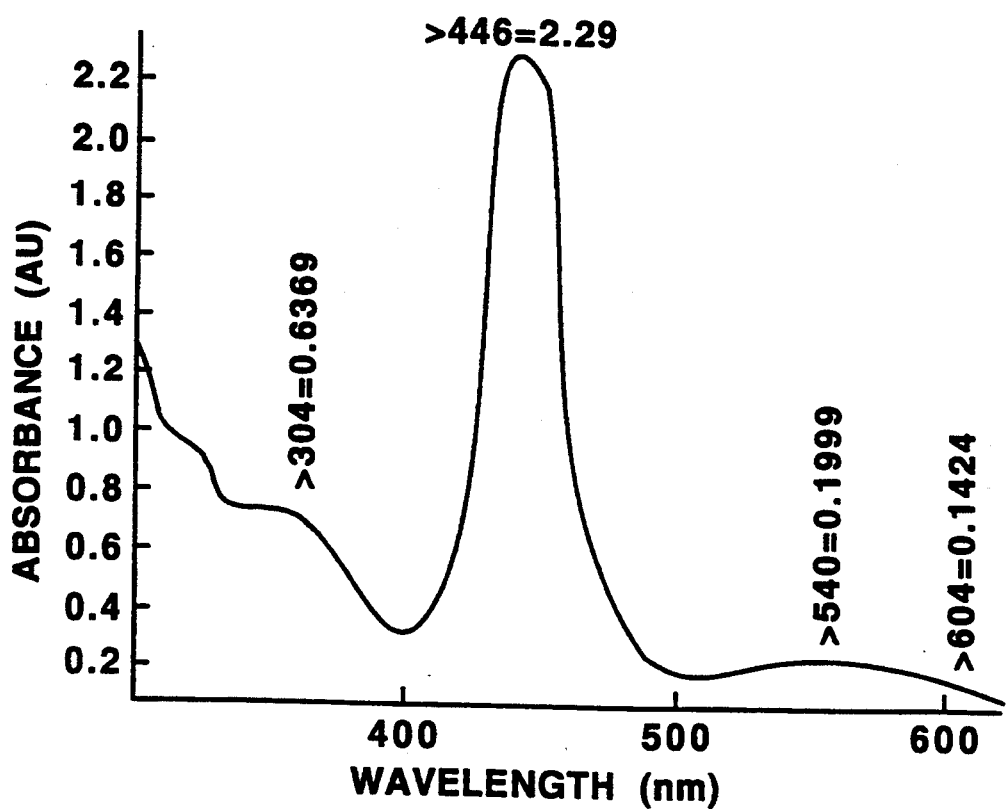
FIG. 7 shows a UV-visible spectrum of the carbon monoxide adduct shown in FIG. 2.

FIG. 2 shows a specific embodiment of a porphyrin metal-thiolate complex in accordance with the present invention. In this embodiment, the crown ether and bridge are as in FIG. 1, the metal is iron (Fe(II)), and the ligand contains a thiolate that is held by the crown ether in axial coordination with the metal. In the presence of carbon monoxide, a carbon monoxide adduct with the complex is formed, as evidenced by the appearance of a Soret band at 446 nm in the UV-visible spectrum, shown in FIG. 7. Preparation of such a complex is discussed further below.

II.A Preparation of porphyrin-crown compounds and complexes.

Figure 3:
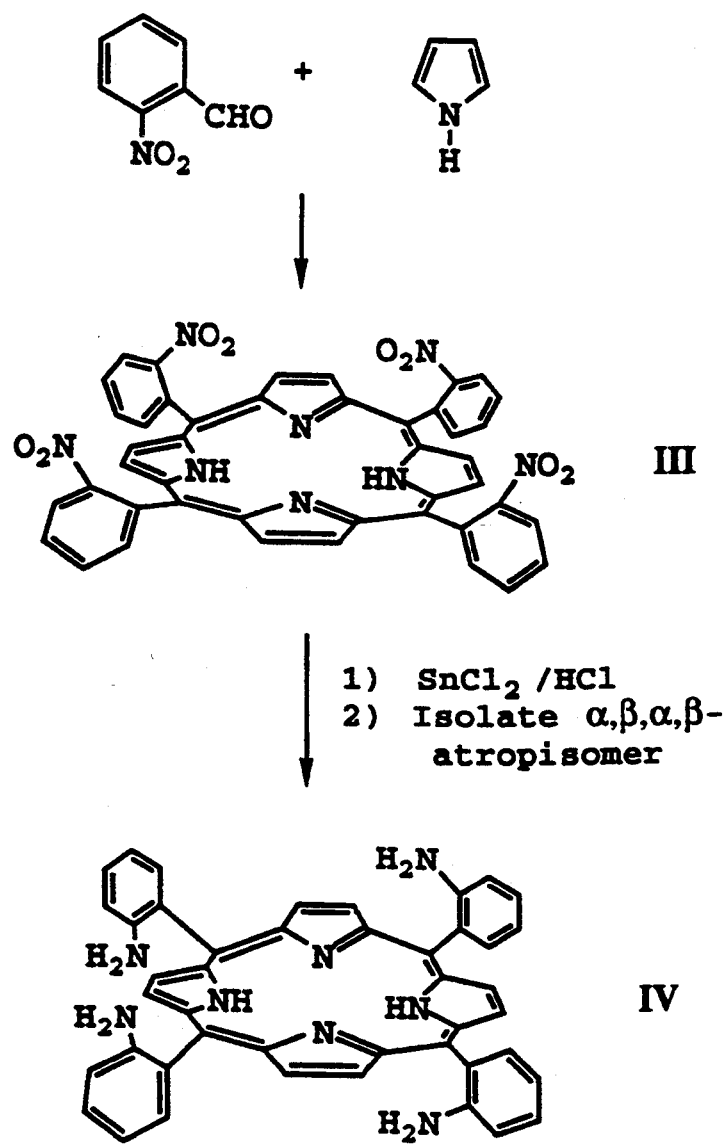
FIG. 3 shows a reaction scheme for preparing porphyrin components for use in synthesis of porphyrin-crown compounds of the present invention.
Figure 4:
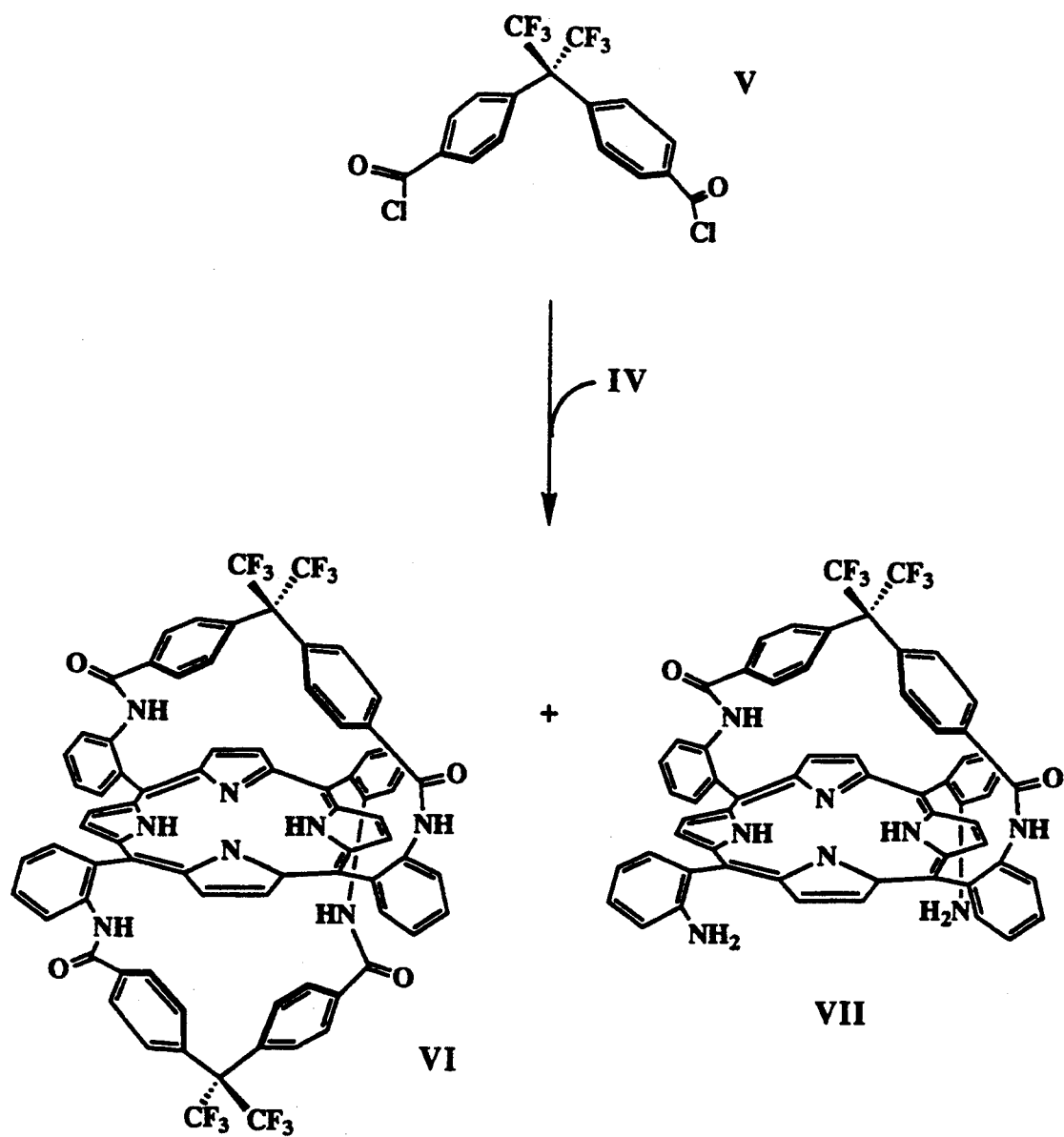
FIGS. 4 and 5 together show a reaction scheme for preparing a bridged porphyrin-crown compound of the present invention.
Figure 5:
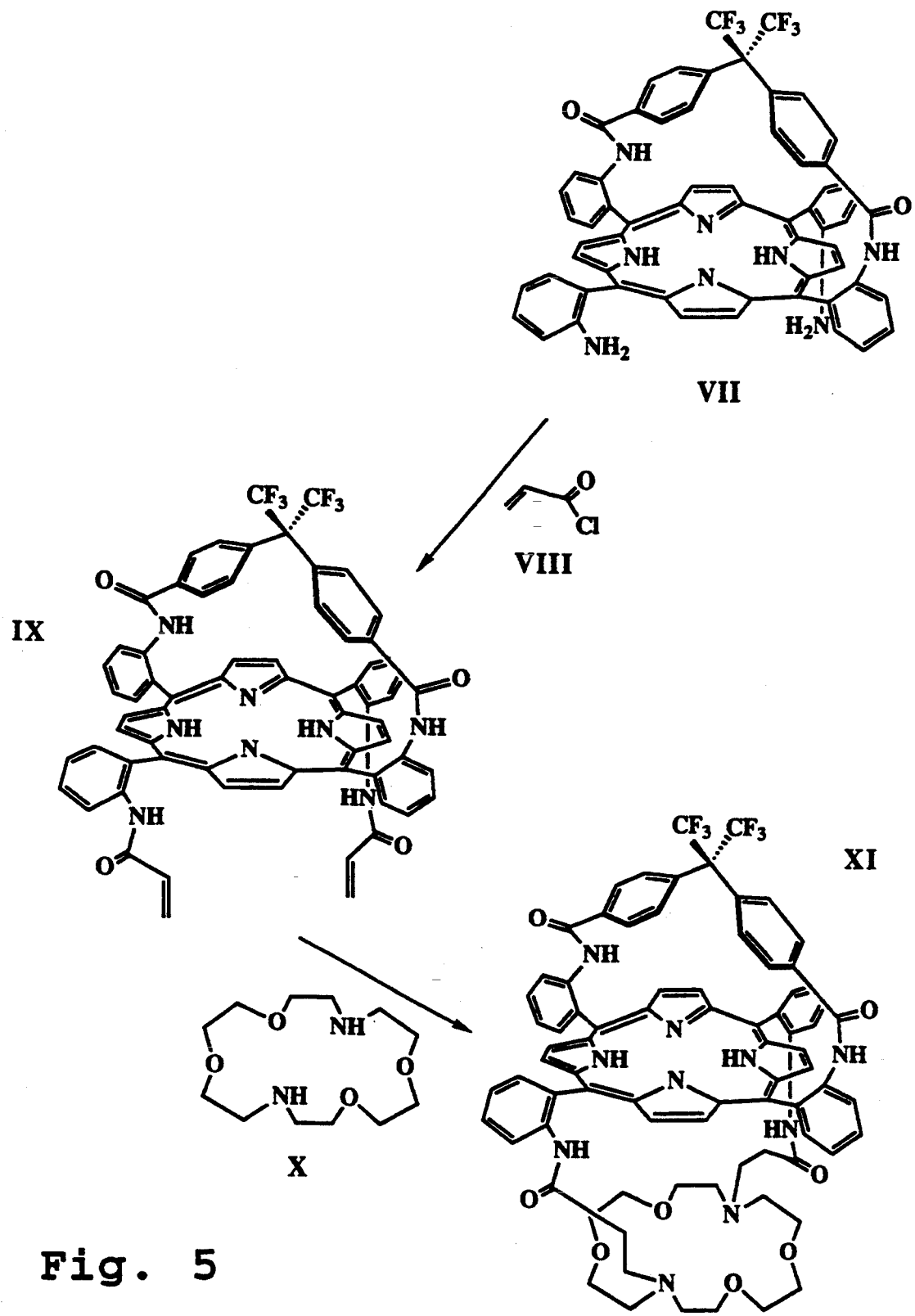

Reaction schemes for preparing a porphyrin-crown (also referred to herein as a bridged porphyrin-crown) in accordance with the present invention are shown in FIGS. 3, 4 and 5. FIG. 3 shows a scheme for preparing meso-$\alpha,\beta,\alpha,\beta$-tetrakis(o-aminophenyl)porphyrin (IV), a starting material for use in the first step of FIG. 4. With reference to FIG. 3, pyrrole is reacted with 2-nitrobenzaldehyde to give meso-tetrakis(o-nitrophenyl)porphyrin (III). This product is reduced using SnCl$_2$ and HCl to give mesotetrakis(o-nitrophenyl)porphyrin (Sorrell, 1980) as a mixture of four atropisomers ($\alpha,\alpha,\alpha,\alpha$; $\alpha,\alpha,\alpha,\beta$, $\alpha,\alpha,\beta,\beta$; and $\alpha,\beta,\alpha,\beta$; ratio$\approx$1:4:2:1). The $\alpha,\beta,\alpha,\beta$-atropisomer is isolated using silica gel chromatography by loading the mixture onto a silica gel column in CH$_2$Cl$_2$ and eluting the $\alpha,\beta,\alpha,\beta$-atropisomer (II) as the first eluting peak using 10% ethyl acetate in CH$_2$Cl$_2$.

With reference to FIG. 4, tetraphenylporphyrin IV is reacted with a slight excess (1.3 equiv) of 2,2-bis(4-carboxyphenyl)hexafluoropropane diacid chloride (V) to produce bridged porphyrin VI. In this reaction, separate solutions of IV and V in CH$_2$Cl$_2$ are added simultaneously under nitrogen atmosphere to a reaction flask over a period of several hours. The reaction is stirred for an additional 24 hours at room temperature, and then the CH$_2$Cl$_2$ is removed under vacuum. The resultant residue is loaded on a silica gel column prepared from a slurry in CH$_2$Cl$_2$ and is eluted using 5% diethyl ether in CH$_2$Cl$_2$. Three components elute from the column: bis-bridged porphyrin VI (first peak, ~40% yield), starting material IV (second peak, <5% yield), and bridged porphyrin VII (third peak, ~39% yield).

In the next step (FIG. 5), bridged porphyrin VII in CH$_2$Cl$_2$ is reacted with acryloyl chloride VIII (2.5 equiv in CH$_2$Cl$_2$) in the presence of 2,6-lutidene (2.3 equiv) to scavenge HCl. Following stirring of the reaction at room temperature for 1 hour, the solvent is evaporated to dryness. The resultant residue is loaded onto a column prepared from a CH$_2$Cl$_2$ slurry and is eluted using 10% diethyl ether in CH$_2$Cl$_2$, thereby providing activated, bridged porphyrin IX.

To obtain bridged porphyrin-crown XI, 1,10-diazo-18-crown-6 (X, 5 equiv) is added to a solution of activated, bridged porphyrin IX (1 equiv in 100% ethanol) under nitrogen atmosphere, and the resultant mixture is refluxed for 4 days, protected from light by aluminum foil. The reaction is then cooled to room temperature and evaporated to dryness, and the resultant residue is dissolved in CH$_2$C$_2$ and loaded onto a neutral alumina column prepared from a CH$_2$Cl$_2$ slurry. Residual starting material is eluted with 10% acetone in CH$_2$Cl$_2$, followed by elution of desired product (XI) using 20% acetone in CH$_2$Cl$_2$. Details of the reactions illustrated in FIGS. 3–5 are given in Example 2.

Figure 14:
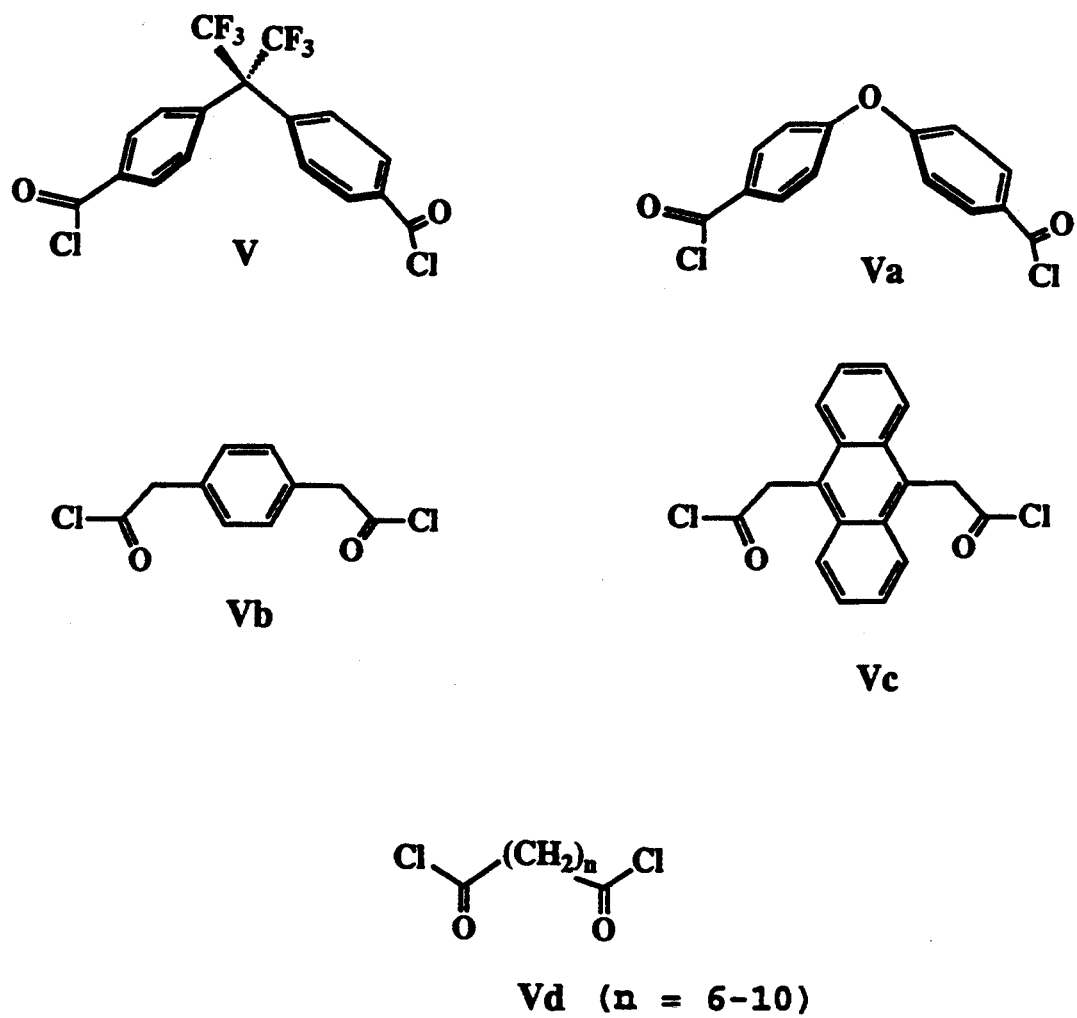
FIG. 14 illustrates bridge reagents for use in preparing bridged porphyrin-crown compounds of the present invention.

Although synthesis of a specific porphyrin-crown compound is described above, it is to be appreciated that a number of other porphyrin-crown compounds can be prepared in accordance with the present invention. In general, a tetraphenylporphyrin starting material such as IV is reacted with a bifunctional bridge reagent having acid chlorides or acid bromides at its ends and capable of forming a covalent bridge between the amino groups of two $\alpha$ or two $\beta$ phenyl groups in the porphyrin. A requisite of the bifunctional bridge reagent is that the resultant bridge sterically hinder $\mu$-oxo dimer formation when a metal ion is bound to the porphyrin ring. For applications in which the compound is to be used as an oxygen carrier, it is preferable that the bridge create a space above the porphyrin ring that is large enough for small molecules such as oxygen or carbon monoxide to bind the porphyrin metal, but is at the same time sufficiently small to hinder or prevent binding of bulky ligands such as imidazole. Exemplary but non-limiting bridge reagents are illustrated in FIG. 14 (although shown as diacid chlorides, the bridge reagents may also have the form of diacid bromides).

Since both sides of the tetraphenylporphyrin starting material are reactive toward the bifunctional bridge reagent, and two equivalents of bridge reagent is usually sufficient to convert all of the tetraphenylporphyrin starting material to a bis-bridge product, the ratio of bridge reagent:porphyrin should be tailored to maximize the yield of the mono-bridged porphyrin. A stoichiometry of about 0.7:1 to 1.4 is preferred. It can be appreciated that the actual yield of mono-bridged porphyrin may vary according to the structure of the bridge reagent used.

Once isolated, the mono-bridged porphyrin is activated using a bifunctional activating agent to introduce spacer arms by which a crown ether (also sometimes referred to herein as a "crown"), defined further below, can be covalently attached. Relatively short spacer arms are preferred, since an important function of the arms is to hold the crown rigidly above the porphyrin ring. Preferably, the activating agent produces a covalent linkage between the crown and the tetraphenylporphyrin phenyl groups that is between 2 and 6, and preferably 3 or 4, atoms in length.

A preferred bifunctional activating agent is an acryloyl halide such as acryloyl chloride or acryloyl bromide. As described above, reaction of mono-bridged porphyrin with acryloyl chloride produces an activated, bridged porphyrin having two vinyl groups. The reactivity of these vinyl groups can then be used to link the activated, bridged porphyrin to a crown ether (e.g., 1,10-diazo-18-crown-6).

An alternative activating agent, for linking the crown ether more closely to the porphyrin ring, is chloroacetyl chloride (or alternatively, bromoacetyl bromide). This bifunctional activating agent can be reacted with a mono-bridged porphyrin under reaction conditions similar to those described above for acryloyl chloride. Only the acyl halide groups react with the free amino groups of mono-bridged porphyrin VII under the reaction conditions employed. The resultant activated, bridged porphyrin contains halomethyl groups that can be reacted with amino groups of a suitable crown ether (e.g., 1,10-diazo-18-crown-6) under well known reaction conditions for displacing a chloride or bromide moiety with an amine to produce a porphyrin-crown in accordance with the present invention.

An important function of the crown in the metalloporphyrin-crown complexes of the present invention is to hold a ligand so that a metal-binding atom in the ligand is axially coordinated to the porphyrin metal ion. Accordingly, any crown ether capable of this function and amenable to synthesis may be used. An exemplary crown ether is 1,10-diazo-18-crown-6, which has a strong binding affinity for primary ammonium ions. Other suitable crown ethers include structures having a 1,10-diazo-18-crown-6 backbone but which are derivatized with additional substituents at backbone carbon atoms (e.g., wherein a pair of oxygen atoms in the backbone are linked by a benzo group rather than by an ethylene bridge). A useful tabulation of crown structures and their affinities for various ions may be found in the article by Izatt et al. ("Thermodynamic and Kinetic Data for Macrocycle Interaction with Cations and Anions", Chem. Rev. 91, 1721-2085 (1991)), which is incorporated herein by reference.

The metal ion M in the metalloporphyrin complexes of the present invention can be any of a number of transition metals including cobalt, iron, manganese, ruthenium, and chromium. Methods for introducing such metals into porphyrin rings are well known in the art; protocols for introducing iron (Fe(II)) or cobalt (Co(II)) are described in Example 3. General metal-insertion protocols may also be found in Smith ("Porphyrins and Metalloporphyrins, K. M. Smith ed., Elsevier Scientific Publishing Co., New York, 1975), for example.

Where the porphyrin-crown complex is to be used to bind oxygen, M is preferably iron or cobalt. Generally, iron (Fe(II)) provides on the order of 100-fold stronger oxygen-binding affinity than does cobalt, but at the same time is more susceptible than cobalt (Co(II)) to irreversible inactivation by oxygen-mediated processes (e.g., $\mu$-oxo dimerization). For applications where the porphyrin-crown complex is to be used in solution, cobalt is preferred, in view of its stability against such inactivation. For solid phase applications, however, iron may be more preferred, since the inactivation processes that can occur in solution occur much more slowly in a solid phase arrangement.

Where the porphyrin-crown complex is to be used to bind carbon monoxide, M is preferably Fe(II).

The ligand to be held by the crown, in axial coordination with the porphyrin metal, should contain (a) a metal-coordinating atom that has a favorable binding affinity (e.g., binding is an exothermic process) for the metal (e.g., a thiolate sulfur atom, an $sp^2$-hybridized nitrogen, or a phenolate oxygen), and (b) a crown-binding group for which the crown has a high affinity (e.g., a primary amine, where the crown is 1,10-diaza-18-crown-6). The metal-coordinating atom and the crown-binding group in the ligand are spaced apart to allow simultaneous binding of the ligand to the metal and the crown. Preferably, the metal-coordinating atom is separated from the crown-binding group by a bridge of 2-4 atoms. In addition, the overall size of the ligand must be small enough to fit in the space between the porphyrin ring and the crown. The suitability of a candidate ligand for use with a particular bridged porphyrin-crown may be qualitatively evaluated in part by molecular modeling (e.g., by use of CPK models).

Figure 6:
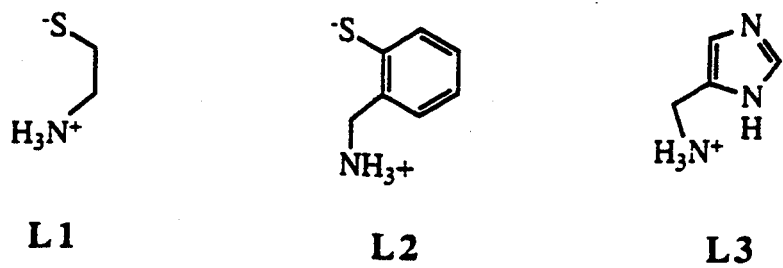
FIG. 6 shows exemplary ligands for a bridged porphyrin-crown of the present invention.

FIG. 6 shows three ligands, L1, L2, and L3, for use in the porphyrin-crown complex of FIG. 1, wherein M is Fe(II). With reference to FIG. 6, ligand L1 contains a thiolate sulfur atom for coordinating to the porphyrin metal, and a protonated primary amino group for binding (being held by) the crown. As illustrated in FIG. 1, the crown of complex I holds the amino group of the ligand via hydrogen bonds between the hydrogen atoms of the protonated amine and heteroatoms of the crown. A ligand similar to L1, but which is bulkier and contains an aromatic ring, is shown at structure L2. A ligand having an $sp^2$-hybridized nitrogen atom for binding the metal is shown at structure L3.

It is also contemplated that the crown can hold a ligand indirectly via a monovalent metal ion that is chelated by the crown. For example, if the crown can bind a potassium ion with high affinity, a ligand having a negatively charged group such as a carboxylate can be held indirectly by the crown via electrostatic interaction with the chelated potassium ion.

According to an important feature of the bridged porphyrin-crown complexes described above, the binding of the crown to the ligand enhances the affinity of the ligand for porphyrin metal M. This is especially advantageous where the metal-binding atom is a thiolate sulfur atom and the metal is Fe(II), as illustrated in Example 4. The degree by which the non-covalent binding of the crown to the ligand stabilizes coordination of the ligand to the metal may be roughly estimated based upon a known binding affinity of the crown for the crown-binding group in the ligand. For example, a crown having a 1,10-diaza-18-crown-6 backbone has an affinity for primary amines of about 7-10 kcal/mol, predicting an enhancement in binding affinity of the porphyrin for the ligand by a factor of about $10^5-10^7$.

Example 4 describes a study in which the carbon monoxide adduct of a porphyrin metal-thiolate complex was formed using 2-mercaptoethylamine as ligand (generated in situ from ethylammonium chloride by the addition of the base, BEMP; see Example 4). To a solution of the Fe(II) complex of bridged porphyrin-crown XI ($\sim$10 $\mu$M) in toluene in a cuvette under inert atmosphere was added a solution of 2-mercaptoethylamine (0.3M in 100% ethanol) to a final concentration of about 1 mM. The cuvette was then covered with a septum, and carbon monoxide gas was passed through the mixture for several minutes.

UV-visible absorption spectroscopy of the resulting solution revealed a new peak at 446 nm (FIG. 7) which is characteristic of the carbon monoxide adduct of a metalloporphyrin-thiolate complex. The new peak was not observed when ethylamine was used instead of 2-mercaptoethylamine, thereby supporting the assignment of the new peak to structure II in FIG. 2. Moreover, the peak was not observed in experiments (a) in which a ligand (ethanethiol in the presence of BEMP) lacking an amino group was used in place of 2-mercaptoethylamine, and (b) in which 2-mercaptoethylamine was used, but bridged porphyrin structure VII (no crown) was used in place of bridged porphyrin-crown XI. These results demonstrate that a crown such as in bridged porphyrin-crown XI can afford significant enhancement in the binding affinity of a thiolate ligand for a porphyrin metal M.

II.B Affinity Measurements

The binding affinities of ligands and small molecules with the metalloporphyrin complexes of the present invention can be measured in solution by UV-visible spectrophotometric titration methods that are well known in the art (e.g., Hashimoto et al., 1982; Linard et al., 1980; Collman et al., 1976).

Typically, although both axial coordination sites of metal M are available for binding, ligand L binds only at the axial site on the crown-side of the porphyrin ring, both because of binding affinity enhancement by the crown and also because of steric encumbrance by the bridge structure on the other side of the porphyrin ring. Thus, ligand binding data can be interpreted in accord with the equilibrium equation:

where MP, L, and MP.L represent metalloporphyrin, ligand, and the metalloporphyrin-ligand complex, respectively, and $K_L$ is the association constant. Ligands that do not conform to the above equilibrium equation because of formation of a di-ligand complex (before saturation of the first ligand-binding site is achieved) are unsuitable for use in the present invention since binding of ligand to the bridge-side of the porphyrin can block the binding of oxygen and carbon monoxide.

It is noted that measuring $K_L$ for a thiolate ligand by the above method may be difficult because spectral changes that occur upon coordination of the thiolate sulfur to the metal may be small. In this case, it may be preferable to include carbon monoxide in the solution to allow determination of $K_L$ using the Soret band of the ligand-metal-carbon monoxide complex.

The oxygen or carbon monoxide binding affinity of a metalloporphyrin-ligand complex is determined in the presence of a pre-selected concentration of ligand, e.g., a concentration sufficient to achieve greater than 99% occupancy of the ligand-binding site, thereby deterring oxygen-mediated degradation of the complex. The pre-selected concentration can be chosen on the basis of a measured value of $K_L$. Oxygen binding data is then interpreted in accord with the equilibrium equation:

$$MP.L + O_2 \xrightleftharpoons{K_{O2}} MP.L.O_2$$

where MP.L, $O_2$, and MP.L.$O_2$ represent the metalloporphyrin-ligand complex, unbound dioxygen, and the dioxygen-bound complex, respectively, and $K_{O2}$ is the equilibrium (affinity) constant. Conveniently, the concentration of $O_2$ is measured as a partial pressure, and the binding affinity is expressed in terms of $P_{(\frac{1}{2})}(O_2)$, the partial pressure of oxygen at which the concentrations of MP.L and MP.L.$O_2$ are equal (note that $P_{(\frac{1}{2})}(O_2)$ is equal to $1/K_{O2}$).

A corresponding equilibrium equation applies to the binding of carbon monoxide, where the binding affinity for carbon monoxide is expressed in terms of $P(\frac{1}{2})(CO)$.

II.C Applications

In one aspect, the bridged porphyrin-crown compounds described above are useful in a method for binding carbon monoxide or oxygen in a liquid. Typically, the liquid is a non-polar solvent such as toluene, $CH_2Cl_2$, chloroform, and the like.

In one embodiment, the method is used in sequestering carbon monoxide in a liquid. For this application, metal M is preferably Fe(II), and the ligand includes a metal-binding atom such as a thiolate group or an $sp^2$-hybridized nitrogen for binding metal M. If oxygen is also present in the liquid, the metal-binding atom is preferably an $sp^2$-hybridized nitrogen (e.g., an imidazole group), since thiolates are susceptible to oxidation. Preferably, the ligand is present at a concentration that affords greater than 99% saturation of the ligand-binding site.

In another embodiment, the method is used to measure the concentration of carbon monoxide in a test liquid. In this application, extinction coefficients at a convenient wavelength for measuring bound carbon monoxide must be known beforehand for the selected metalloporphyrin-ligand complex and its carbon monoxide adduct. In addition, the binding affinity ($P_{(\frac{1}{2})}(CO)$) must be known for the metalloporphyrin under the particular test conditions. Accordingly, a known concentration of metalloporphyrin complex (including ligand) is added to the test liquid, and the concentration of carbon monoxide adduct is determined spectrophotometrically by applying Beer's law. The measured adduct concentration, the total concentration of metalloporphyrin in the liquid, and the known value of $P_{(\frac{1}{2})}(CO)$ constitute sufficient information for deriving the concentration of carbon monoxide in the liquid.

As noted above, if oxygen is also present in the liquid, the metal-binding atom in the ligand is preferably an $sp^2$-hybridized nitrogen. However, where little or no oxygen is present, a thiolate as the metal-binding atom is advantageous since the resultant carbon monoxide adduct gives rise to a strong absorbance band in a distinctive region of the UV-visible spectrum (i.e., the metalloporphyrin-ligand complex does not absorb in that region in the absence of carbon monoxide), thus affording enhanced sensitivity.

In related embodiments, the metalloporphyrin complexes are useful for sequestering oxygen and for measuring the concentration of oxygen in the liquid, by the same general approaches as described above for carbon monoxide. For these applications, the metal-binding atom in the ligand is preferably an $sp^2$-hybridized nitrogen.

From the description above, it can be appreciated that the present invention provides a novel way of delivering any of a variety of axial ligands to a porphyrin metal, by non-covalent means. In previous approaches for solution applications, such axial ligands have been covalently attached, at high expense, to the porphyrin compound, or have been included in a large excess relative to the porphyrin compound to ensure high occupancy of the axial site. These limitations are overcome by the present invention, which, as described above, provides a porphyrin-crown compound that is effective to enhance the binding affinity of even a ligand that binds iron weakly, such as a thiolate.

III. Water-Soluble Oxygen Carriers

In another aspect, the present invention includes water-soluble oxygen carrier complexes. In general, the complexes include a meso-$\alpha,\alpha,\alpha,\alpha$-tetrakis(o-propanoylamino)phenylporphyrin in which the 3-carbons of the propanoyl groups are each covalently bound to an amine nitrogen. As will be seen below, the complexes generally contain at least two such amine nitrogens to each of which are covalently bound one or two of the propanoyl 3-carbons. Preferably, the amine nitrogens are tertiary or quaternary amine nitrogens.

Figure 9:
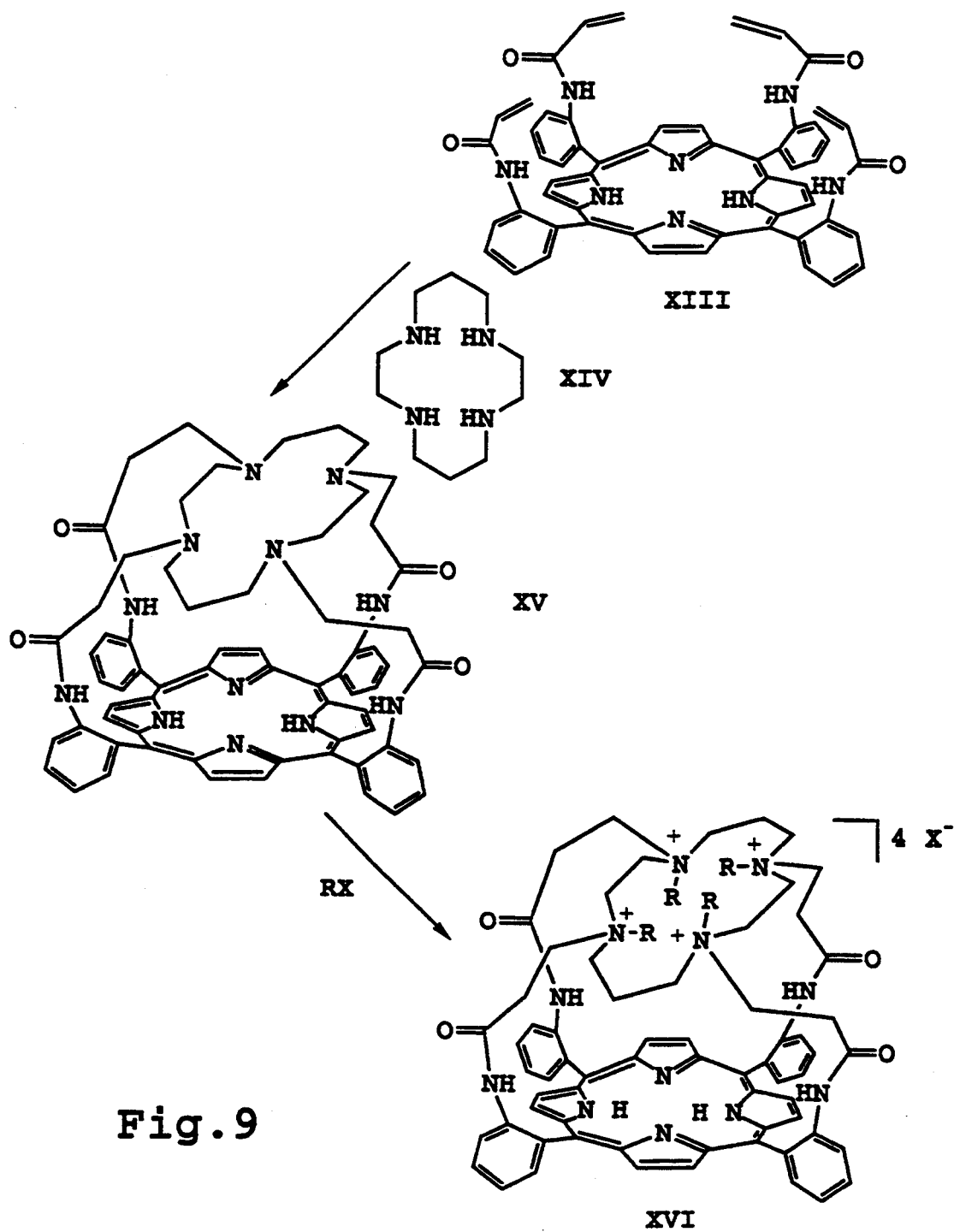
FIGS. 9–13 show a reaction schemes for preparing water-soluble oxygen carriers in accordance with the present invention.
Figure 11:
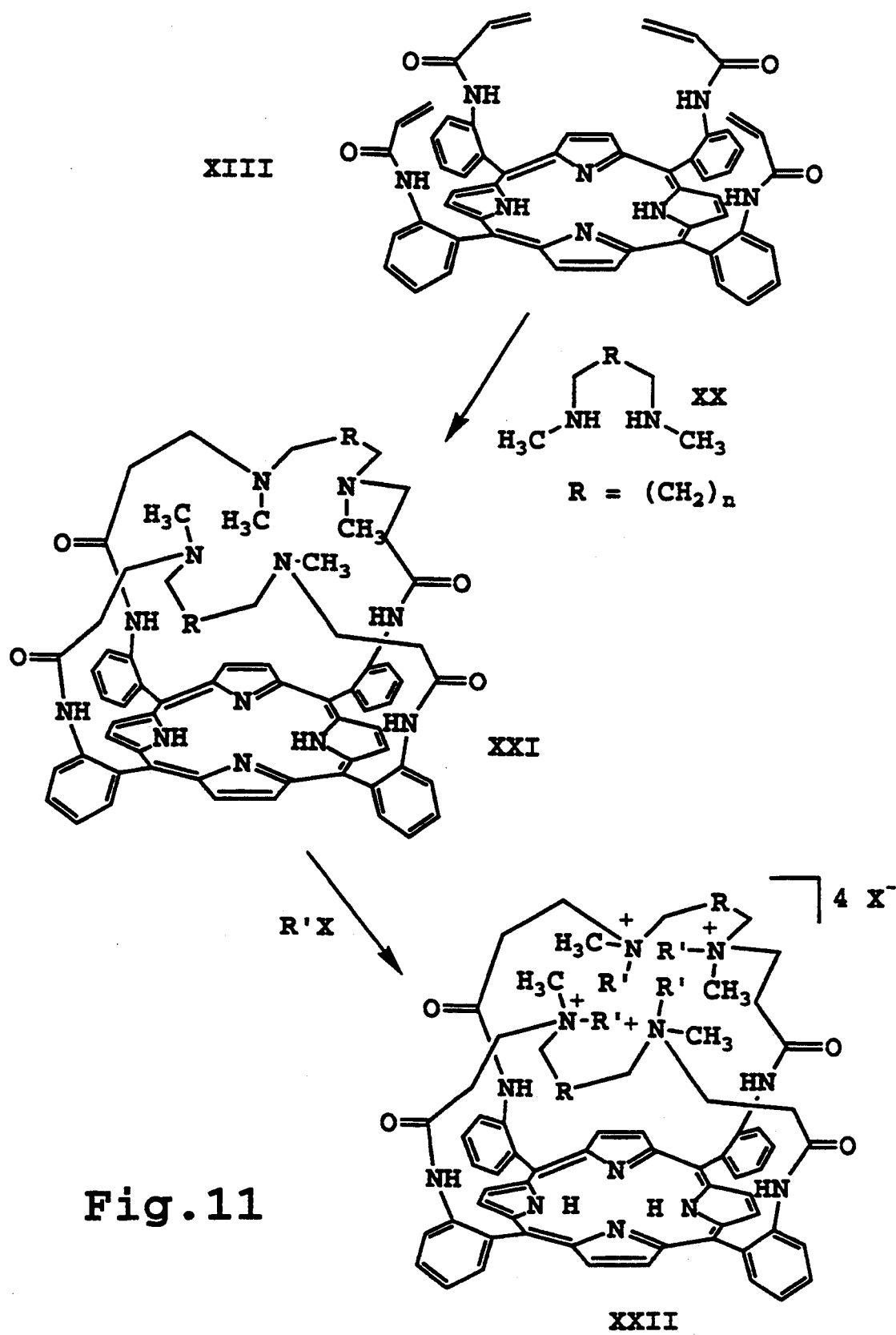

In one preferred embodiment, the compound contains four amine nitrogens wherein the 3-carbons of all four propanoyl groups are each covalently bound to a different one of the amine nitrogens. Exemplary compounds of this type are illustrated in FIGS. 9 and 11.

Figure 10:
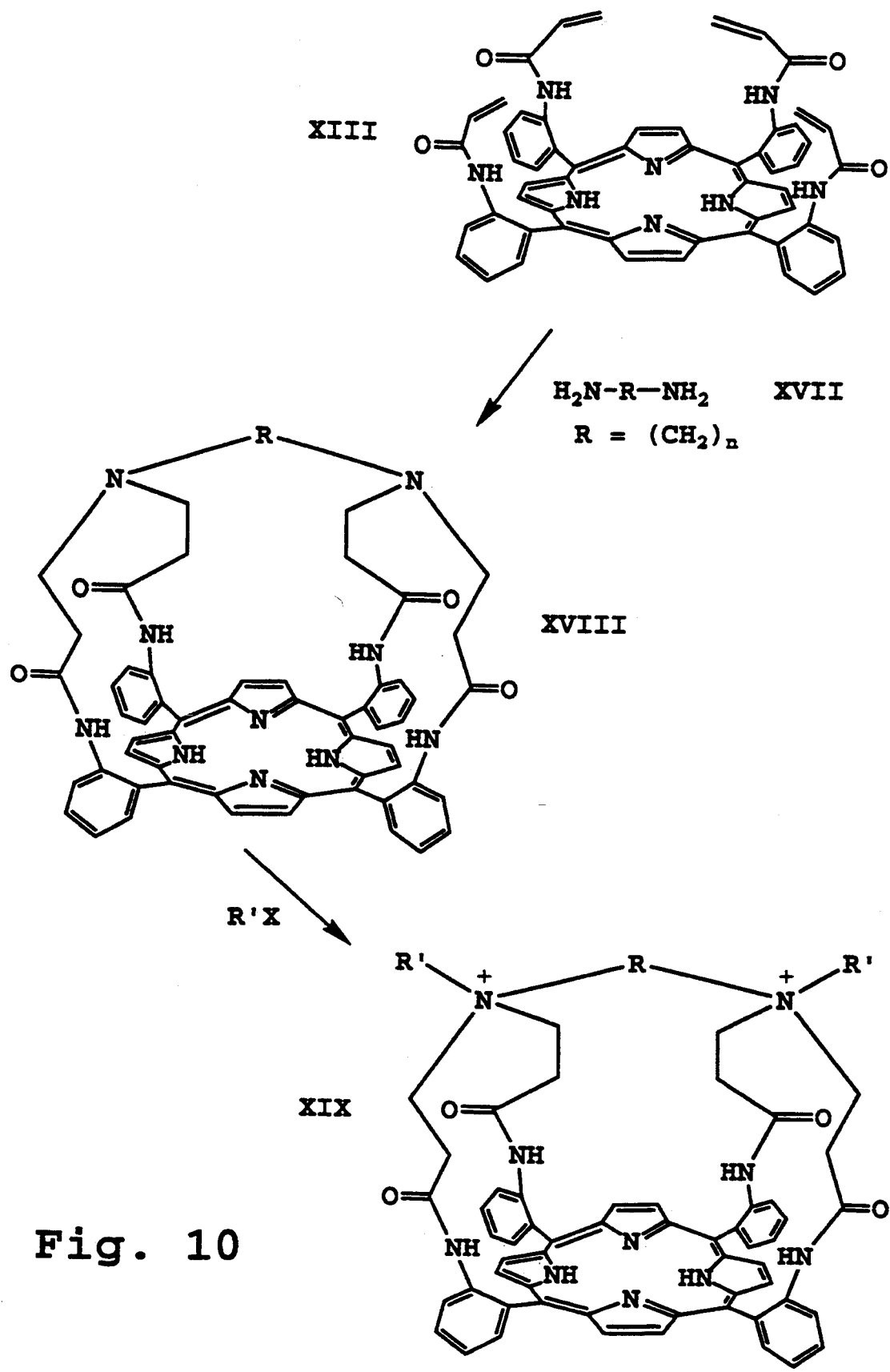
Figure 12:
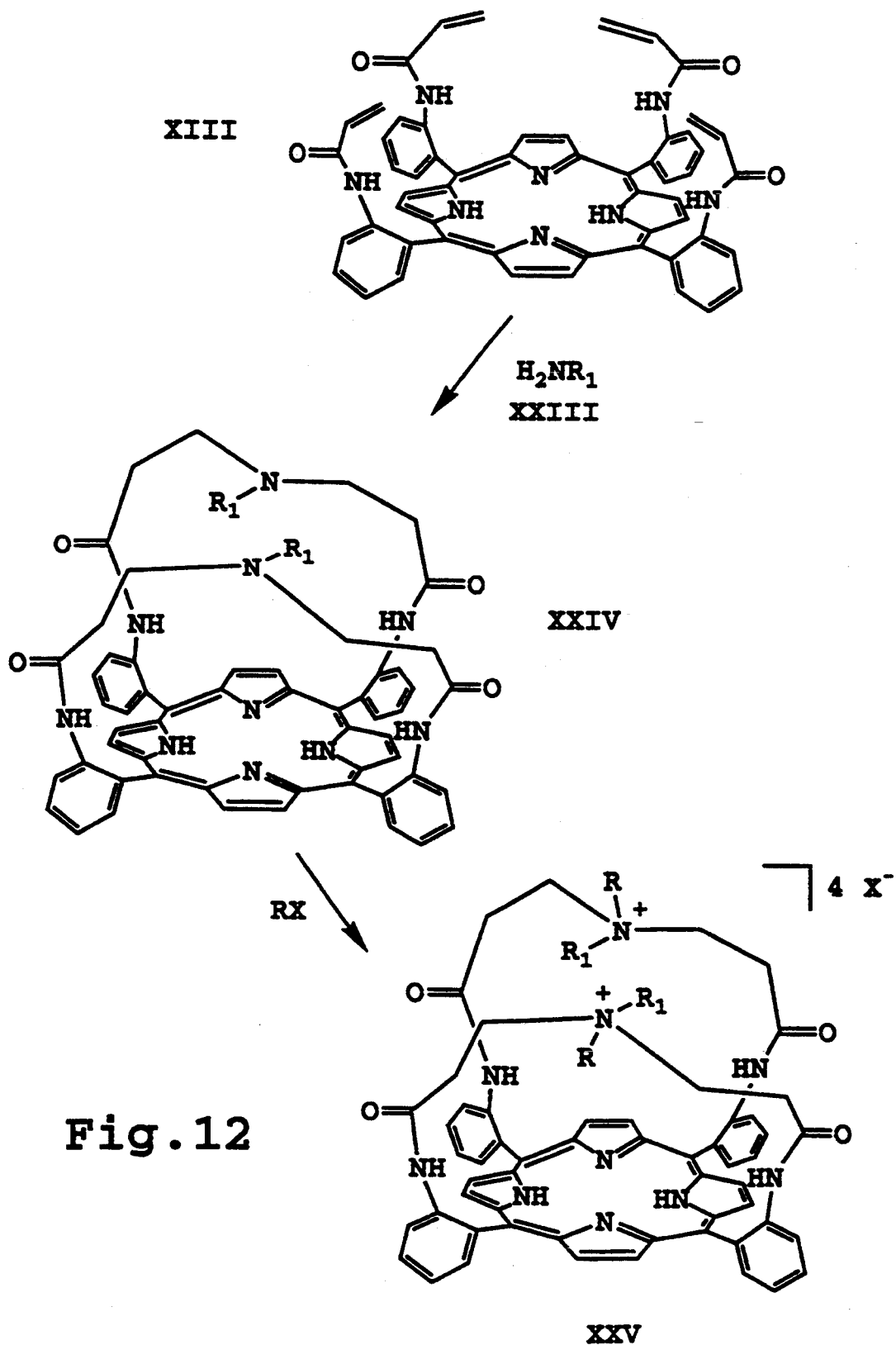

In another preferred embodiment, the 3-carbons of a first pair of propanoyl groups are each covalently bound to a first amine nitrogen, and the 3-carbons of a second pair of propanoyl groups, different from the first pair, are each covalently bound to a second amine nitrogen. Exemplary compounds of this type are illustrated in FIGS. 10 and 12.

The complexes also include a metal that is bound to the pyrrole nitrogens of the porphyrin, and a ligand L that is bound as an axial ligand to the metal, thereby blocking $\mu$-oxo dimer formation.

For the sections below, the term "3-carbon" refers to C-3 of an acrylamino ($CH_2$=$CHC$(=$O$)$NH$—) or propanoylamino (RCH$_2$CH$_2$C(=O)NH—) group, where the carbonyl carbon in such groups is referred to as the 1-carbon (C-1). Likewise, the term "3-amino group" denotes an amino group attached to C-3 of an acrylamino or propanoylamino group.

III.A Preparation

Water-soluble porphyrin compounds of the present invention may be synthesized from α,α,α,α-tetrakis(o-aminophenyl)porphyrin XII, an isomer wherein four phenyl amino groups are located on the same side of the porphyrin ring. In a method of the invention, XII is reacted with acryloyl chloride or acryloyl bromide to produce an activated, tetraacrylamide porphyrin. This activated porphyrin is then reacted with an amine to produce a meso-α,α,α,α-tetrakis(o-propanoylamino)-phenylporphyrin derivative containing amino groups attached to the 3-carbons of the o-propanoyl groups (this derivative is also termed herein "meso-α,α,α,α-tetrakis(o-(3-aminopropanoylamino)phenyl)porphyrin". Suitable amines include, for example, cyclams (i.e., cyclopolyaminoalkanes), diaminoalkanes, di(monoalkylamino)alkanes, and monoamines including ammonia. Optionally, the 3-amino groups of the derivative may be converted to quaternary amines by alkylation. The compounds thus formed provide highly water-soluble porphyrin compounds that are useful as oxygen carriers when a metal M (preferably cobalt) is inserted into the porphyrin ring.

As detailed further below, a variety of amines can be used to prepare compounds of the present invention. Preferably, the selected amine is effective to produce a porphyrin derivative containing at least two propanoyl groups that are linked by a nitrogen-containing bridge, since such linking prevents isomerization (e.g., see structures XV, XVIII, XXI, and XXIV in FIGS. 9-12). In addition, such linking can enhance oxygen affinity in the corresponding metalloporphyrin complex by sterically hindering the binding of bulky ligands (e.g., imidazole) to the axial coordination site to be occupied by dioxygen.

It will be appreciated that an advantage of using quaternary amines to enhance water-solubility (see compounds XVI, XIX, XXII, XXV, and XXVIII, for example) is that the positive charge at each nitrogen atom is not affected by changes in environmental pH. In contrast, the average charge on a non-quaternary alkyl amine is diminished in alkaline conditions, particularly when the pH is near or greater than the pKa of the amine.

Figure 8:
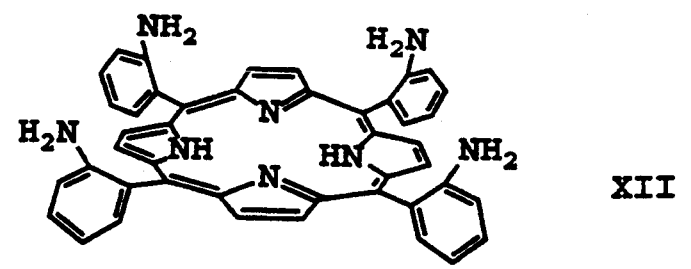
FIG. 8 shows a reaction scheme for producing an activated tetraphenylporphyrin of the present invention.
Figure 8:
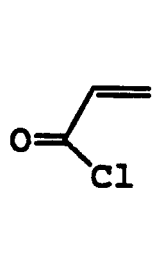
Figure 8:
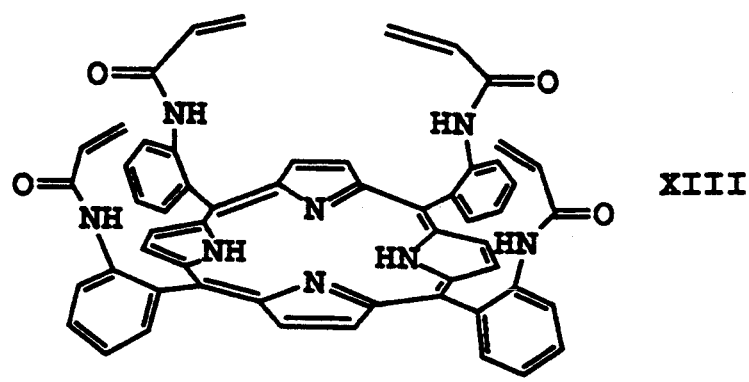

A synthetic scheme for preparing an exemplary water-soluble oxygen carrier in accordance with the present invention is shown in FIGS. 8 and 9. With reference to FIG. 8, to a solution of α,α,α,α-tetrakis(o-aminophenyl)porphyrin (1 equivalent) in CH$_2$Cl$_2$ under inert atmosphere at room temperature is added a solution of about 4 to 4.5 equivalents of acryloyl chloride (or acryloyl bromide) in CH$_2$Cl$_2$, followed by the addition of about 4 to 4.5 equivalents of base (e.g., 2,6-lutidine). Following stirring of the reaction mixture at room temperature for about 1 hour, the solvent is evaporated to dryness. The residue, dissolved in a small volume of CH$_2$Cl$_2$, is loaded onto a silica gel column prepared from a CH$_2$Cl$_2$ slurry and eluted with 20% acetone/CH$_2$Cl$_2$.

With reference now to FIG. 9, purified product XIII (1 equivalent) is reacted with excess cyclam 1,4,8,11-tetraazacyclotetradecane XIV (e.g., about 5 equivalents) in 100% ethanol. The mixture is heated at reflux for several days under inert atmosphere, with the reaction flask wrapped in aluminum foil to exclude light. The reaction is then cooled and evaporated to dryness to remove the solvent. The resultant residue is chromatographed using a neutral alumina column, wherein the sample is loaded in CH$_2$Cl$_2$ and eluted using 20% acetone/CH$_2$Cl$_2$. Details of synthesis procedures for preparing porphyrin-cyclam XV are given in Example 5. A procedure for preparing a porphyrin-cyclen compound which is similar to XV are given in Example 6.

More generally, the compounds of the type shown at XV and XVI in FIG. 9 are formed from reacting XIII and a cyclopolyaminoalkanes that contains four ring nitrogens. The ring nitrogens in the cyclopolyaminoalkane are preferably joined to each other by alkyl linking groups, i.e., (CH$_2$)$_n$, where n is 2–4, and preferably 2 or 3.

The water solubility of resultant tetraamine XV can be enhanced by treatment with an alkylating agent RX, such as methyl iodide or ethyl iodide, where R is preferably an activated alkyl group RX in which R is an alkane containing 1–5 carbon atoms. In brief, tetraamine XV is reacted with an excess of the alkylating agent RX in a solvent such as dimethylformamide (DMF) for a time sufficient to convert the amine nitrogens to quaternary amines (XVI). Preferably, the extent of reaction is monitored using cation-exchange high performance liquid chromatography, where the appearance of positively charged reaction products can be monitored using a porphyrin absorbance peak for detection. Following removal of the DMF solvent under reduced pressure, the alkylated product can be purified preparatively from the reaction mixture by standard extraction procedures, e.g., by extraction of the reaction mixture with water or aqueous base to selectively extract the positively charged reaction product(s), followed by preparative cation exchange chromatography, if necessary.

The methods of synthesis described above can be adapted to produce other water-soluble compounds in accordance with the present invention. For example, as illustrated in FIG. 10, activated porphyrin XIII can be reacted with a diaminoalkane XVII (NH$_2$—R—NH$_2$, where R is preferably (CH$_2$)$_n$ and n=1–6; e.g., 1,2-diaminoethane) to produce porphyrin compound XVIII. Preferably, the diaminoalkane is present in the reaction in moderate excess relative to the amount of porphyrin XIII (e.g., about a 5-fold excess) so that the desired product is obtained with minimal polymerization. Subsequent treatment of XVIII with an alkylating agent (e.g., methyl iodide) by the general methods set forth above produces a water-soluble compound XIX that contains two quaternary amines linked to each other by an alkyl bridge.

With continued reference to FIG. 10, compounds XVIII and XIX each contain two pairs of propanoyl groups, a first pair whose 3-carbons are bound to a first amine nitrogen, and a second pair whose 3-carbons are bound to a second amine nitrogen. The amine nitrogens are covalently joined by a linking group R, defined as for FIG. 9 above. Details of a synthetic procedure for preparing compounds of this type are given in Example 7.

Similarly, as illustrated in FIG. 11, reaction of XIII with a di(monoalkylamino)alkane XX (e.g., N,N'-dimethyl-1,2-diaminoethane) produces porphyrin compound XXI, which, upon alkylation by methods noted above, can be converted into compound XXII, where the R' groups are preferably alkyl groups containing 1-5 carbon atoms. Details of a synthetic procedure for preparing this type of compound are given in Example 8. It can be seen that each of the four amine nitrogens in XXI and XXII is joined covalently to a second amine nitrogen by a linking group which is preferably an alkyl chain containing 1-6 carbon atoms, and preferably 2 or 3 carbon atoms.

Alternatively, as illustrated in FIG. 12, activated porphyrin XIII can be reacted with an alkyl amine XXIII ($H_2NR_1$, where R and $R_1$ are preferably alkyl groups containing 1-5 carbon atoms; e.g., methylamine) to produce XXIV, which can be alkylated as above to produce water-soluble porphyrin XXV. The compounds of this type are similar to those shown in FIG. 10, except that the amine nitrogens are not joined to each other by a linking group.

Figure 13:
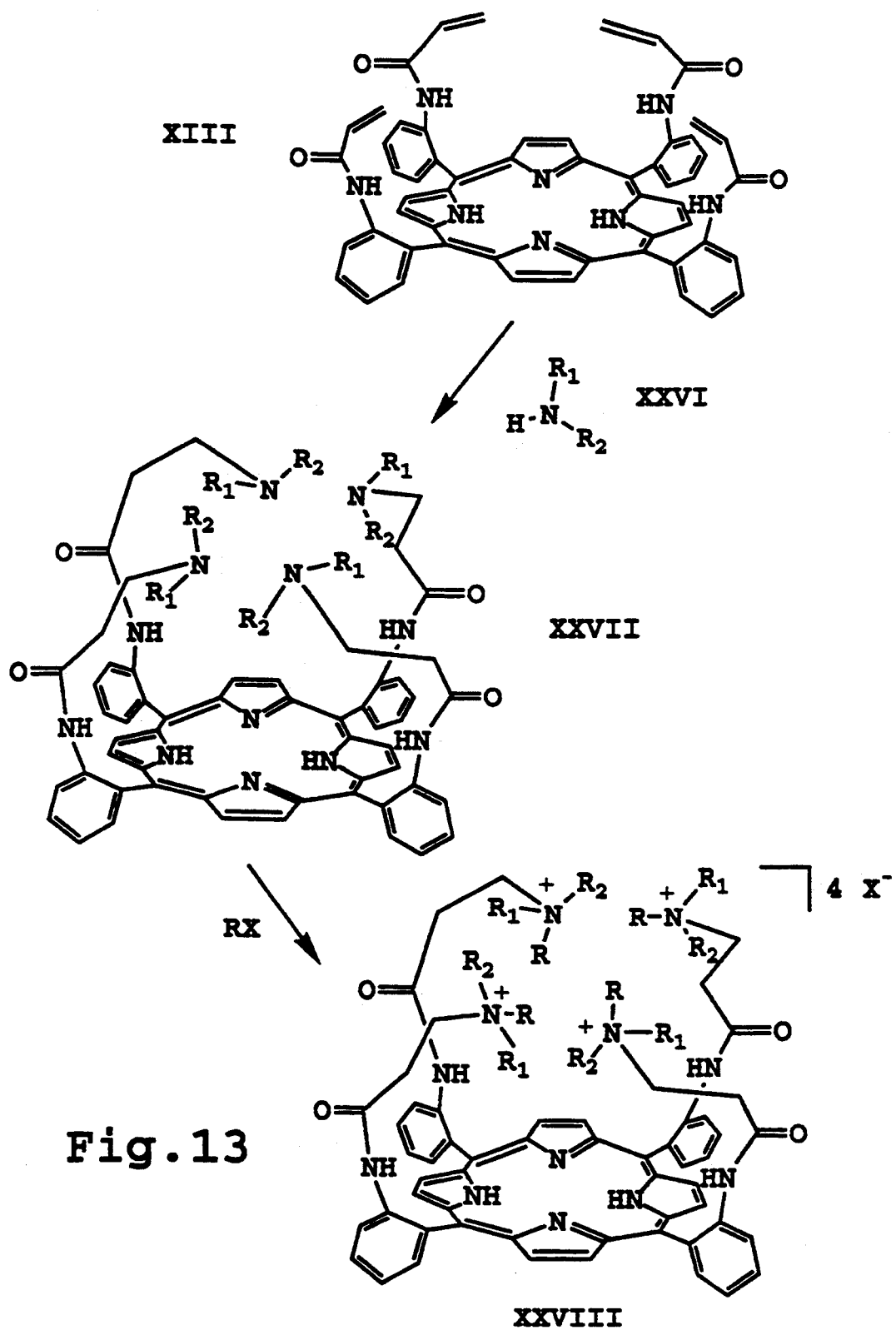

A reaction scheme for preparing another water-soluble porphyrin is shown in FIG. 13. Here, activated porphyrin XIII is treated with an excess of a primary or secondary amine (or ammonia) (XXVI) to add separate amino groups to the 3-carbons of the acrylamide moieties. Subsequent alkylation of the product, XXVII, affords water-soluble porphyrin XXVIII, where R, $R_1$, and $R_2$ are preferably alkyl groups containing 1-5 carbon atoms.

Metal M may be inserted into the porphyrin ring of the water soluble porphyrin compounds above by well known methods. Where M is to be iron or cobalt, the procedures described in Example 3 may be used, except that dimethylformamide is preferably used as the solvent rather than THF or benzene/THF, and the temperature of the DMF is preferably maintained at about 60°-80° C. More conveniently, metal insertion can be performed in aqueous medium using the method described in Labat et al. (1989). Briefly, the porphyrin compound is heated with 5-10 equivalents of a metalating agent (e.g., Co(II) acetate, Mn(II) acetate, or ammonium Fe(II) sulfate hexahydrate) in water at about 80° C., pH of 5 to 8, for a period of about 1-2 hours.

The course of the metal reaction is monitored by UV-visible spectroscopy. Following removal of the solvent under reduced pressure, residual metalating agent is removed from the porphyrin compound using a cation exchange column (e.g., Amberlite CG-50 (H+ form); see Smith and Lower, 1991). Alternatively, but less preferably, the porphyrin compound may be isolated from the aqueous solution by extraction with generous amounts of a water-immiscible solvent such as methylene chloride or chloroform.

The metalation step may also be performed prior to the alkylation step, wherein the meso-$\alpha,\alpha,\alpha,\alpha$-tetrakis-(o-(3-aminopropanoylamino)phenyl)porphyrin derivative is metalated with anhydrous $FeBr_2$ or $CoCl_2$ as in Example 3. The resultant metal complex is then alkylated as described above, thereby producing a water-soluble oxygen carrier. A drawback of this approach is that metal may be lost from the porphyrin during alkylation.

It is noted that whereas the inner face of the metalloporphyrin is sterically encumbered by the propanoylamino moieties, thereby deterring $\mu$-oxo dimer formation, protection of the open face of the porphyrin (the side opposite the propanoylamino moieties) requires the presence of a ligand L which can bind metal M on the open face of the porphyrin. Furthermore, since the porphyrin compounds described in this section (section III) are typically for use in aqueous solvent, the ligand must be water-soluble. Suitable water-soluble ligands include substituted as well as non-substituted nitrogen-containing aromatic heterocycles such as imidazoles, pyridines, and pyrazines, and, less preferably, primary, secondary, and tertiary amines. Preferably, L is 1-methylimidazole.

Typically the ligand is present in the porphyrin solution in about a 100- to a 1000-fold excess relative to the porphyrin. Preferably, the concentration of ligand achieves greater than 99% occupancy of the axial site on the open side of the porphyrin ring. For choosing a ligand concentration to achieve such an occupancy level, the affinity constant of the metalloporphyrin for the ligand can be determined by methods well known in the art, as discussed above in section II.B.

In addition, because the positive charge in a quaternary amine is pH-independent, the quaternary amine-containing water-soluble oxygen carriers of the present invention are soluble over a wide pH range. Preferably, pH conditions greater than 10 or less than 4 should be avoided, since high pH can promote base-catalyzed loss of the ammonium groups (i.e., via elimination), and low pH can promote loss of metal M. A pH of about 6 to 8 is preferred.

It can be appreciated from the methodologies described above that the compounds described in this section (section III) can be immobilized on a solid support using an alkylation step such as described above, where RX refers to an suitably activated support, or alternatively, via a ligand L which has been immobilized on a solid support.

The invention also contemplates use of the oxygen carriers of the invention for binding oxygen in non-aqueous solvents such as toluene, dichloromethane, methanol and the like.

III.B Applications

In one aspect, water-soluble oxygen carriers of the present invention are useful in a method for extracting oxygen from an oxygen-containing fluid. The method includes exposing an oxygen-containing fluid to an oxygen-binding complex such as described in section III.A above, so that an oxygenated carrier is formed. Optionally, the method can include removal of bound oxygen from the oxygenated carrier so that the carrier can be used again to extract additional oxygen.

In a specific embodiment, the oxygen-carrier is contained in an enclosed, circulating liquid wherein the oxygen-binding state of the carrier is modulated electrochemically; i.e., the porphyrin metal is interconverted between a high oxygen affinity state (e.g., Fe(II) or Co(II)) and a low oxygen affinity state (e.g., Fe(III) or Co(III)). The carrier is circulated in an oxygen-binding state to a region in the enclosure that is in contact (e.g., by way of an oxygen-permeable membrane) with an oxygen-containing fluid. The fluid can be a liquid or a gas. An oxygenated carrier is thus formed which is then passed through an electrode compartment effective to oxidize the carrier to a higher oxidation state having low oxygen affinity. The liquid is then passed through an oxygen unloading region to collect oxygen released from the low affinity carrier. The cycle is completed by passage of the fluid through a second electrode compartment effective to reduce the carrier back to the oxygen-binding form. The circulating fluid may additionally include an electrocatalyst, such as a water-soluble ferrocene (see, for example, U.S. Pat. No. 5,017,274)

or the like, to facilitate interconversion of the high and low oxygen affinity states in the oxygen carrier. Exemplary methods for extracting oxygen as above are described in U.S. Pat. No. 4,952,289.

By such methods, the oxygen carrier may be used for purifying an oxygen-containing gas, such as for removal of $O_2$ from $N_2$, or for producing $O_2$ in purified form.

In summary, the invention described in section III above provides oxygen-carrier porphyrin compounds that are water-soluble and that can be prepared in good yield. In a particularly advantageous aspect, the oxygen-carriers contain propanoylamino groups that are covalently linked by an amine-containing bridge, thereby deterring isomerization. The compounds can be used for extracting oxygen from oxygen-containing fluids and for providing oxygen gas in purified form.

The following examples illustrate, but are not in any way intended to limit the scope of the invention.

EXAMPLES

Reagents

Reactants and solvents were obtained from commercial sources and were used as received unless noted otherwise. Iron dibromide was from Strem. Solvents were distilled under a nitrogen atmosphere. Methylene chloride was distilled from $P_2O_5$. Methanol was dried and distilled from $Mg(OMe)_2$. Benzene, diethyl ether, tetrahydrofuran (THF), and toluene were distilled from sodium benzophenone ketyl. Dry dimethylformamide was obtained by reduced pressure distillation from BaO. Thionyl chloride was distilled from triphenylphosphite. 2,6-Lutidine was stored over KOH and distilled from BaO. Silica gel supplied by E. M. Science (Type 7736) was used for flash chromatography. $^1H$ NMR spectra were obtained on a Nicolet NMC-300 or Varian XL-400 Spectrometer and referenced to residual proton solvents. Mass spectra were performed at the Mass Spectrometry Facility at the University of California, San Francisco. UV-visible spectra were recorded on a Hewlett-Packard 8452A Diode Array Spectrophotometer equipped with a 7470A plotter.

Example 1

$\alpha,\beta,\alpha,\beta$-Tetrakis(o-aminophenyl)porphyrin (IV)

Compound IV was prepared using the method of Sorrell (1980) to prepare a mixture of atropisomers (steps A and B) and isolating the $\alpha,\beta,\alpha,\beta$-atropisomer by silica gel chromatography (step C). Quantities were scaled according to the amount of product desired.

A. Meso-tetrakis(o-nitrophenyl)porphyrin (III). One hundred grams of 2-nitrobenzaldehyde (0.6 mole) were dissolved in 1700 mL of glacial acetic acid in a 3-L three-neck round-bottom flask fitted with an efficient condenser and a dropping funnel. The solution was then heated just to its boiling point while being vigorously stirred with a magnetic stirring bar. Forty-six mL of pyrrole (47.6 g, 0.71 mole) were added dropwise to the solution at such a rate that the reaction did not become uncontrollable. The resultant black mixture was allowed to reflux for 30 minutes before being cooled in an ice bath to 35° C. (Tars form if the solution is cooled below this temperature.) During the cooling process, 250 mL of chloroform were slowly added to prevent the formation of tars. (The chloroform boils if the solution is too hot). The purple crystalline product was filtered by suction, washed with five 100-mL portions of $CHCl_3$, and dried at 100° C. overnight. Yield: 17.3–22.0 g (13.2–16.8%). UV-Vis (DMF): 409, 518, 551, 594, and 652 nm.

B. Meso-tetrakis(o-aminophenyl)porphyrin (mixture of atropisomers). A 3-L beaker was charged with 12.0 g (0.015 mole) of the product (III) from the previous step and 600 mL of concentrated HCl (sp gr 1.18). To this was added a solution of 50 g (0.22 mole) of $SnCl_2.H_2O$ (reagent grade) dissolved in 50 mL of concentrated hydrochloric acid. The solution was stirred for 90 minutes at room temperature. The beaker was then placed in a hot water bath atop a hot plate-magnetic stirrer. The temperature of the bath was raised to 65° C. in a 10-minute period and held between 65 and 70° C. for 25 minutes. Good stirring was maintained during this time. (Heating above 75° C. results in a low yield of impure product.) The beaker was then placed in an ice bath and swirled to bring the contents to room temperature. The solution was then neutralized by the slow addition (20–30 min) of about 600 mL of concentrated ammonium hydroxide. (Caution: This reaction is highly exothermic.) After cooling to room temperature, the highly basic solution (pH > 10) was stirred for at least 12 hours with 1 L of $CHCl_3$.

The organic layer was separated and the aqueous phase was transferred to a 4-L separatory funnel. Water (1.5 L) was added and the solution was extracted with three 150-mL portions of $CHCl_3$. The combined extracts were washed with 1 L of dilute $NH_4OH$, which washings in turn were extracted with two 50-mL portions of chloroform. The combined organic portion was evaporated to 600 mL on a rotary evaporator and then filtered by suction. The filtrate and washings were concentrated to 250 mL, 150 mL of 95% ethanol containing 10 mL of conc. aqueous $NH_3$ was added, and the solvent slowly evaporated until the remaining volume was about 200 mL. The sides of the flask were washed down with chloroform and 100 mL of ethanol was added. The volume was then reduced to 75 mL, and the resulting crystals were filtered, washed with five 10-mL portions of 95% ethanol, and dried in an oven at 100° C. for several hours. Yield: 6.6–8.1 g (65–80%) of a mixture of atropisomers.

C. $\alpha,\beta,\alpha,\beta$-Atropisomer (IV). In a typical procedure, 10 g of the atropisomer mixture prepared as in the previous step were dissolved in 1 L of $CH_2Cl_2$ and loaded onto a 30×10 cm silica gel column equilibrated in $CH_2Cl_2$. The desired $\alpha, \beta, \alpha, \beta$-atropisomer comprising about 12% of the atropisomer mixture, was eluted as the first eluting atropisomer using 10% ethyl acetate in $CH_2Cl_2$. The column effluent was carefully monitored by TLC analysis (silica gel) using benzene-ether (1:1). Under these TLC conditions, the atropisomers have the following $R_f$ values: 0.77 ($\alpha,\beta,\alpha,\beta$), 0.64 ($\alpha,\alpha,\beta,\beta$), 0.43 ($\alpha,\alpha,\alpha,\beta$), and 0.04 ($\alpha,\alpha,\alpha,\alpha$). Fractions containing the $\alpha,\beta,\alpha, \beta$-atropisomer were combined and evaporated to dryness, typically providing 1.0–1.2 g of IV.

To recover additional $\alpha,\alpha,\alpha,\alpha$-atropisomer, the atropisomers that had remained on the column were eluted using acetone-ether (1:1). The eluted atropisomers were pooled, concentrated to dryness under vacuum, and dissolved in reagent-grade toluene (50 mL per gram of solid atropisomer mixture) in a three-neck round-bottom flask fitted with a nitrogen inlet and reflux condenser. The mixture was refluxed for about 6 hours under dry nitrogen atmosphere to generate an equilibrium mixture of atropisomers (including the $\alpha,\beta,\alpha,\beta$-atropisomer). The dark slurry was allowed to cool, and the toluene was then removed under vacuum. The resulting solid was chromatographed again as in the previous paragraph to recover additional α,β,α,β-atropisomer.

Example 2
Synthesis of Bridged Porphyrin-Crown XI

A. Diacid Chloride V. 2,2-Bis(4-carboxyphenyl) hexafluoropropane (5.0 g, 12.7 mmol), thionyl chloride (30 mL), and two drops of DMF were added to a 50 mL round bottom flask under $N_2$ atmosphere. The mixture was heated at reflux for 3 h until all of the solid had dissolved. The excess $SOCl_2$ was evaporated under vacuum to give diacid chloride V as a light tan solid (4.29 g, 78.4%). $^1H$ NMR ($CDCl_3$) δ: 8.16 (d, J=8.7 Hz, 4H), 7.54 (d, J=8.5 Hz, 4H).

B. Bridged Porphyrin VII. The following reaction was performed under rigorously dry conditions. All glassware was dried at 120° C. and cooled in the antechamber of a glove box. α,β,α,β-Tetra(o-aminophenyl)porphyrin IV (1.625 g, 2.42 mmol) was dissolved in $CH_2Cl_2$(100 mL) in the glove box. Diacid chloride V (1,362 g, 3.17 mmol) was dissolved in $CH_2Cl_2$ (100 mL) in a flask. A 1 L three-neck round-bottom flask containing triethylamine (2.0 mL) and $CH_2Cl_2$(100 mL) was fitted with a $N_2$ inlet. The porphyrin and diacid chloride solutions were each drawn into 100 mL gas-tight syringes. The two reactants were added dropwise at the same rate into the three neck flask under a $N_2$ atmosphere using a syringe pump (Harvard Apparatus). After the addition was complete (6 h), the solution was stirred for an additional 24 h at room temperature. The $CH_2Cl_2$ solution was then evaporated to dryness, and the residue was dissolved in $CH_2Cl_2$, loaded onto a silica gel column prepared from a $CH_2Cl_2$ slurry, and eluted using 5% $Et_2O/CH_2Cl_2$. The first eluting band was a bis-bridged porphyrin VI (1.334 g, 39.9%), wherein both pairs of diagonally opposing phenyl groups had become bridged; the second band was starting material (IV; 0.072 g); and the third band was the product, bridged porphyrin VII (0.967 g, 38.9%).

Characterization of bridged porphyrin VII: $^1H$ NMR ($CDCl_3$) δ: 8.93 (d, J=4.8 Hz, 4H); 8.89 (d, J=4.8 Hz, 4H); 8.73 (d, J=8.1 Hz, 2H); 8.52 (d, J=7.7 Hz, 2H); 7.92 (t, J=7.9 Hz, 2H); 7.75–7.70 (m, 4H); 7.60 (t, J=7.8 Hz, 2H); 7.16 (t, J=7.8 Hz, 2H); 7.08 (d, J=7.9 Hz, 2H); 6.65 (s, 2H); 6.20 (s, 8H); 3.41 (s, 4H); −2.65 (s, 2H). MS (LSIMS+): m/e=1031 (M+H)+ for $C_{61}F_6H_{40}N_8O_2$. Analysis: Calc. for $C_{61}F_6H_{40}N_8O_2 \cdot CH_2Cl_2$: C, 66.73H, 3.83; 3.79; N, 10.04; F, 10.21. Found: C, 66.98; H, 3.83; N, 9.90; F, 9.83.

Characterization of bis-bridged porphyrin VI: $^1$NMR ($CDCl_3$) δ: 8.91 (s, 8H); 8.76 (d, J=8.3 Hz, 4H); 8.33 (d, J=7.1 Hz, 4H); 7.93 (t, J=7.8 Hz, 4H); 7.70 (t, J=7.5 Hz, 4H); 6.59 (s, 4H); 6.22 (m, 16H); −2.58 (s, 2H). MS (LSIMS+): m/e=1387 (M+H)+ for $C_{78}F_{12}H_{46}N_8O_4$. Analysis: calc. for $C_{78}F_{12}H_{46}N_8O_4$: C, 67.53; H, 3.34; N, 8.08; 16.43; found: C, 67.46; H, 3.31; N, 8.13; F, 16.23. UV-vis ($CH_2Cl_2$): 424 (Soret), 516, 550, 588, 644 nm.

C. Activated Bridged Porphyrin IX. Bridged porphyrin VII (0.825 g, 1.76 mmol) was dissolved in $CH_2Cl_2$(45 mL) in a flask. To this solution at room temperature under $N_2$ was added acryloyl chloride (V; 0.181 g, 2.0 mmol) in 6 mL of $CH_2Cl_2$ and then 2,6-lutidine (0.188 g, 1.76 mmol). The reaction mixture was stirred at room temperature for 1 h, and the solvent was evaporated to dryness. The residue was dissolved in $CH_2Cl_2$, loaded onto a silica gel column prepared from a $CH_2Cl_2$ slurry, and eluted with 10% $Et_2O/CH_2Cl_2$. Removal of solvent from combined fractions gave activated bridged porphyrin VI (0.636 g) in 67.3% yield. $^1H$ NMR ($CDCl_3$) δ: 8.94 (d, J=4.8, 4H); 8.82 (d, J=4.8 Hz, 4H); 8.72 (d, J=8.1 Hz, 2H); 8.53 (d, J=6.9 Hz, 2H); 7.94 (t, J=7.7 Hz, 2H); 7.85 (m, 4H); 7.75 (t, J=7.6 Hz, 2H); 7.52 (t, J=7.6 Hz, 2H); 6.65 (s, 2H); 6.58 (s, 2H); 6.20 (s, 8H); 5.81 (d, J=16.8 Hz, 2H); 5.09–4.90 (m, 4H); −2.68 (s, 2H). MS (LSIMS+): m/e=1139 (M+H)+ for $C_{67}F_6H_{44}N_8O_4$. Analysis: calc. for $C_{67}F_6H_{44}N_8O_4 \cdot 3/4\ CH_2Cl_2$: C, 67.94; H, 3.41; N, 9.36; F, 9.52; found: C, 67.83; H, 3.85; N, 9.19; F, 9.14.

D. Bridged Porphyrin-Crown. Activated bridged porphyrin IX (0.579 g, 0.508 mmol) was dissolved in 100% ethanol (125 mL). To this solution under $N_2$ was added 1,10-diazo-18-crown-6 (X, 0.666 g, 2.54 mmol). The reaction mixture was heated at reflux under $N_2$ atmosphere for 4 days, with the flask wrapped in aluminum foil. The reaction was then cooled to room temperature and evaporated to dryness. The resultant residue was loaded onto a neutral alumina column prepared from a $CH_2Cl_2$ slurry. Residual starting material was eluted with 10% acetone/$CH_2Cl_2$, and the desired product (XI) was eluted with 20% acetone/$CH_2Cl_2$ (0.546 g, 76.7% yield).

Example 3
Metal Insertion

Fe insertion. In a typical insertion reaction, bridged porphyrin-crown (40 mg) and 2,6-lutidine (0.2 mL) was added to a boiling solution of benzene and tetrahydrofuran (20 mL, 1:1) in a glove box. The oxygen concentration of the glove box was continually monitored and maintained at less than 1 ppm. Anhydrous $FeBr_2$ (100 mg) was added and the reaction mixture was heated at reflux for about 30 min until the reaction was complete as indicated by UV-vis spectroscopy (i.e., the disappearance of the 4 Q-bands of the metal-free porphyrin). The solvents were evaporated under vacuum, and the residue was redissolved in tetrahydrofuran/benzene (1:10) and loaded onto an alumina column (Activity 1 neutral $A_2O_3$, manufactured by Woelm, 1 cm×10 cm). The product was eluted with methanol/THF/benzene (1:1:10) and stored as a lyophilized solid. The Fe(II) porphyrin complex was obtained in nearly quantitative yield.

Cobalt Insertion. A solution of a porphyrin-containing compound (40 mg), anhydrous $CoCl_2$ (100 mg), and 2,6-lutidine (0.2 mL) in tetrahydrofuran (THF, 20 mL) is heated under reflux under a $N_2$ atmosphere. The reaction is monitored by UV-vis spectroscopy as above and is complete after about 2 h. The THF is removed under vacuum and the remaining solid is dissolved in benzene (50 mL). The benzene solution is washed with dilute ammonia solution (3×30 mL), dried with $Na_2SO_4$, filtered, and evaporated to dryness. The residue is loaded on a silica gel column and the product is eluted with acetone/methylene chloride (1:5). The excess solvents are removed to give quantitatively-metalated product.

Example 4
Formation of an Fe(II)-CO Complex of Bridged Porphyrin-Crown XI The following steps were performed in a glove box containing a nitrogen atmosphere. To a cuvette containing a ∼10 μM solution of the Fe(II) complex of bridged porphyrin-crown XI in toluene (5 mL) was added a solution (~17 μL) of 2-mercaptoethylammonium chloride (ligand, 0.3 M) and base (2-tert-butylimino-2-diethylaminol,3-dimethylperhydro-1,3,2-diazaphosphorine, "BEMP"; 0.3M) in 100% ethanol, so that the final concentrations of ligand and base were about 1 mM. Note that the base, BEMP, was included to promote formation of the zwitterionic form of 2-mercaptoethylamine. The cuvette was then covered with a septum, and carbon monoxide gas was bubbled through the solution for 5 minutes by needle through the septum.

UV-visible spectroscopic analysis of the solution revealed a new absorbance peak at 446 nm (FIG. 7), indicating the formation of a ferrous-CO porphyrin complex (structure II at FIG. 2). In control experiments, the peak at 446 nm was not observed when either bridged porphyrin VII (no crown) was used in place of XI, or ethanethiol (no ammonium ion) or ethylamine (no thiol) was used in place of 2-mercaptoethylammonium chloride.

Example 5

Porphyrin-Cyclam XV

A. Meso-$\alpha,\alpha,\alpha,\alpha$-tetrakis(o-aminophenyl)porphyrin XII was prepared by the method of Lindsey (1980) from the atropisomer mixture of Example 1, step B. Reagent quantities were scaled according to the amount of product desired.

Reagent-grade benzene (85 mL) and 36 g of silica gel were added to a 250-mL 3-neck round-bottom flask fitted with a nitrogen inlet and reflux condensor. This was immersed in an oil bath maintained at 75°–80° C., with magnetic stirring and a steady flow of benzene-saturated dry nitrogen gas. After 2 h, 1 g of the mixture of atropisomers was added to the flask. After an additional 20 h, the dark slurry was cooled to room temperature and then poured into a 53-mm diameter chromatography column. The residual undesired atropisomers were eluted with benzene-anhydrous ether (1:1) until the eluent became pale red in color (about 200 mL), and then acetone-ether (1:1) was used to elute the $\alpha,\alpha,\alpha,\alpha$-atropisomer (XII). The column effluent was carefully monitored by TLC analysis ( silica gel, benzene-ether (1:1)). $\alpha,\alpha,\alpha,\alpha$-Atropisomer XII eluted after the $\alpha,\alpha,\alpha,\beta$-atropisomer. $^1$H NMR (Me$_2$SO-d$_6$)-d$_6$) $\delta$8.79 (s,8H), 7.69–6.97 (m,16H), 4.62 (s, 8H), −2.78 (s, 2 H); UV-Vis (DMF): 648, 590, 553,516, 415 nm.

B. $\alpha,\alpha,\alpha,\alpha$-Tetrakis (o-acrylamidophenyl)porphyrin (XIII). To a solution of XII (0.500 g, 0.74 mmol) in CH$_2$Cl$_2$ (45 mL) at room temperature under nitrogen atmosphere was added acryloyl chloride (0.268 g, 2.96 mmol) in 6 mL of CH$_2$Cl$_2$ and then 2,6-lutidine (0.349 g, 3.26 mmol) . After the reaction mixture was stirred at room temperature for 1 hour, the solvent was evaporated to dryness. The residue was loaded onto a silica gel column prepared from a CH$_2$Cl$_2$ slurry and eluted with 20% acetone/CH$_2$Cl$_2$. Fractions containing desired product XIII were pooled and evaporated to dryness, providing XIII (0.272 g) in 41.2% yield. $^1$H NMR (CDCl$_3$) $\delta$: 8.86 (s, 8H); 7.95 (d, J=7.2 Hz, 4H); 7.88 (t, J=7.7 Hz, 4H); 7.56–7.46 (m, 8H); 6.94 (s, 4H); 5.93 (d, J =17.0 Hz, 4H); 5.07(b, 8H); −2.76 (s, 2H).

C. Porphyrin-Cyclam XV. To a solution of XIII (100 mg, 0.11 mmol) in 100% ethanol (30 mL) under nitrogen atmosphere was added 1,4,8,11-tetraazacyclotetradecane (XIV, 112 mg, 0.56 mmol). The reaction mixture was heated at reflux for 4 days under nitrogen atmosphere, with the reaction flask wrapped in aluminum foil. The reaction was cooled to room temperature and evaporated to dryness. The resultant residue was loaded onto a neutral alumina column prepared from a CH$_2$Cl$_2$ slurry. The desired product (XV) was eluted with 20% acetone/CH$_2$Cl$_2$ (36 mg, 29.4% yield). $^1$H NMR (CDCl$_3$) $\delta$: 10.1 (s, 4H); 8.96 (d, J=8.0 Hz, 4H); 8.83 (s, 4H); 8.79 (s, 4H); 7.79 (t, J=7.2 Hz, 4H); 7.51 (d, J=7.4 Hz, 4H); 7.32 (t, J=7.4 Hz, 4H); 2.19–2.12 (m, 8H); 2.02 (b, 8H); 1.65 (b, 8H); 0.90–0.88 (m, 4H); 0.29 (b, 8H); −2.74 (s, 2H).

Example 6

Porphyrin-Cyclen

To a solution of 88 mg $\alpha,\alpha,\alpha,\alpha$-tetrakis(o-acrylamidophenyl)porphyrin (XIII; Example 5B) in methanol (25 ml) was added 44 mg cyclen (1,4,7,10-tetraazacyclododecane), and the resultant mixture was refluxed under nitrogen atmosphere with stirring for 68 hours. Following removal of the methanol solvent under reduced pressure, the residue was dissolved in dichloromethane, filtered, and passed through a column of neutral alumina using 2% methanol in dichloromethane as eluent. Yield: 73 mg. Mass spectrum: M+1=1063.6.

Example 7

Porphyrin-Baskets XVIII

To a solution of 200 mg $\alpha,\alpha,\alpha,\alpha$-tetrakis-(o-acrylamidophenyl)porphyrin (XIII; Example 5B) in methanol (25 ml) was added 19.7 μL N,N'-diaminopropane, and the resultant mixture was refluxed under nitrogen atmosphere with stirring for 48 hours. Following removal of the methanol solvent under reduced pressure, the residue was dissolved in dichloromethane, filtered, and passed through a column of neutral alumina using 2% methanol in dichloromethane as eluent. The product had the structure shown at XVIII in FIG. 10, where R=(CH$_2$)$_n$ and n=3. Yield: 113 mg (52%). Mass spectrum: M+1=965.4.

The analogs of XVIII where n=2 and 4 were prepared from 200 mg XIII by the procedure above using ethylenediamine (15.8 μL, n=2) and 1,4-diaminobutane (23.7 μL, n=4) instead of 1,3-diaminopropane. For the n=2 product, the yield was 135 mg (63% yield). Mass spectrum: M+1=951.1. For the n=4 compound, the yield was 107 mg (49% yield). Mass spectrum: M+1=979.5.

Example 8

Porphyrin XXI (n=2).

The procedure in Example 7 was repeated using 23.8 μL N,N'-dimethylethylenediamine in place of N,N'-dimethylaminopropane, thereby forming XXI (FIG. 11, n=2). Yield: 58 mg. Mass spectrum: M+1=1067.5.

Although the invention has been described with respect to particular embodiments, it will be appreciated that various changes and modifications can be made without departing from the invention.

It is claimed:

1. A method of forming a water-soluble oxygen carrier comprising:
    reacting meso-$\alpha,\alpha,\alpha,\alpha$-tetrakis(o-aminophenyl)porphyrin with acryloyl chloride or acryloyl bromide to produce a tetraacrylamide porphyrin;

reacting said tetraacrylamide porphyrin with an amine to produce a meso-α,α,α,α-tetrakis(o-(3-aminopropanoylamino)phenyl)porphyrin;

inserting into the porphyrin, a metal selected from the group consisting of iron and cobalt.

2. The method of claim 1, wherein said amine is a cyclam.

3. The method of claim 1, wherein said amine is a di(monoalkylamino) alkane.

4. The method of claim 1, wherein said amine is a diaminoalkane.

5. A water-soluble oxygen carrier comprising:
a meso-α,α,α,α-tetrakis(o-propanoylamino)phenylporphyrin in which the 3-carbons of the propanoyl groups are each covalently bound to an amine nitrogen; and
iron or cobalt is bound to the pyrrole nitrogens of the porphyrin.

6. The oxygen carrier of claim 5, said carrier containing four amine nitrogens, wherein the 3carbons of all four propanoyl groups are each covalently bound to a different one of said nitrogens.

7. The oxygen carrier of claim 6, wherein said amine nitrogens are part of a cyclam ring.

8. The oxygen carrier of claim 6, wherein a first pair of said amine nitrogens are joined covalently by a first linking group, and a second pair of said amine nitrogens, different from the first pair, are joined covalently by a second linking group.

9. The oxygen carrier of claim 5, wherein the 3-carbons of a first pair of propanoyl groups are each covalently bound to a first amine nitrogen, and the 3-carbons of a second pair of propanoyl groups, different from the first pair, are each covalently bound to a second amine nitrogen.

10. The oxygen carrier of claim 9, wherein the first and second amine nitrogens are joined covalently by a linking group.

11. The oxygen carrier of claim 5, wherein said amine nitrogens are tertiary amines.

12. The oxygen carrier of claim 5, wherein said amine nitrogens are secondary amines.

13. The oxygen carrier of claim 5, wherein said metal is Co(II).

14. The oxygen carrier of claim 5, wherein said metal is Fe(II).

* * * * *